(12) United States Patent
Johnson et al.

(10) Patent No.: US 8,616,213 B2
(45) Date of Patent: Dec. 31, 2013

(54) EARPLUG INSERTION DEVICE

(75) Inventors: Shawn Matthew Johnson, Portland, OR (US); John Matthew Johnson, Portland, OR (US); Joshua Ingvald Kenneth Johnson, Portland, OR (US)

(73) Assignee: J3 Group, LLC, Portland, OR (US)

( * ) Notice: Subject to any disclaimer, the term of this patent is extended or adjusted under 35 U.S.C. 154(b) by 1265 days.

(21) Appl. No.: 12/268,750

(22) Filed: Nov. 11, 2008

(65) Prior Publication Data
US 2009/0266369 A1  Oct. 29, 2009

(51) Int. Cl.
*A61F 5/37* (2006.01)
*A61F 11/00* (2006.01)
*A61F 13/00* (2006.01)
*H04R 25/00* (2006.01)
*H04R 25/02* (2006.01)
*A61B 7/02* (2006.01)
*A61M 1/00* (2006.01)
*A61M 3/00* (2006.01)
*A61M 31/00* (2006.01)
*A61M 37/00* (2006.01)

(52) U.S. Cl.
USPC ........... 128/864; 128/846; 128/857; 181/128; 181/129; 181/130; 181/135; 604/27; 604/28; 604/43; 604/93.01; 604/514; 604/515

(58) Field of Classification Search
USPC ......... 128/830, 839, 840, 846, 857, 864–868; D24/106; 181/128–130, 135; 604/27, 604/28, 43, 93.01, 514, 515
See application file for complete search history.

(56) References Cited

U.S. PATENT DOCUMENTS

| 2,393,340 | A | * | 1/1946 | Stanton ........................ | 128/864 |
| 3,506,008 | A | | 4/1970 | Huck | |
| D294,063 | S | | 2/1988 | Smith | |
| 5,312,415 | A | * | 5/1994 | Palermo ....................... | 606/108 |
| 5,531,703 | A | | 7/1996 | Skwarek et al. | |
| 5,609,164 | A | * | 3/1997 | Dyrud et al. ................. | 128/864 |
| 5,957,136 | A | | 9/1999 | Magidson et al. | |
| 6,006,857 | A | | 12/1999 | Leight et al. | |
| 6,224,573 | B1 | | 5/2001 | Yeager et al. | |
| 6,659,103 | B2 | * | 12/2003 | Tiemens ....................... | 128/864 |
| D550,655 | S | | 9/2007 | Falco | |
| 7,362,875 | B2 | * | 4/2008 | Saxton et al. ................ | 381/322 |
| 7,699,056 | B2 | * | 4/2010 | Tran et al. ..................... | 128/831 |
| 7,715,572 | B2 | * | 5/2010 | Solomito et al. ............. | 381/72 |
| 7,922,755 | B2 | * | 4/2011 | Acosta et al. ............... | 623/1.11 |
| 2003/0029458 | A1 | * | 2/2003 | Tlemens ....................... | 128/864 |

FOREIGN PATENT DOCUMENTS

| WO | 9102504 | 3/1991 |
| WO | 9214427 | 9/1992 |

* cited by examiner

*Primary Examiner* — Patricia Bianco
*Assistant Examiner* — Brandon L Jackson
(74) *Attorney, Agent, or Firm* — Jared S. Goff

(57) ABSTRACT

An earplug insertion device can include a housing that is configured to hold a first earplug and a second earplug. The device can also include an ejection mechanism that can be configured to respond to a first user force by ejecting the first earplug from the device in a first ejection motion. The ejection mechanism can also being configured to respond to a second user force by ejecting the second earplug from the device in a second ejection motion.

24 Claims, 31 Drawing Sheets

EARPLUG INSERTION DEVICE

BACKGROUND

Existing earplugs for noise attenuation can include a cylindrical plug of, for example, elastically deformable foamed plastic material. Such earplugs are generally considered comfortable and effective hearing protectors. Unlike hearing protectors in the form of earmuffs, such earplugs are not bulky when used and the earplugs generally do not cause inconvenient perspiration. Nevertheless, it has been found that many people experience discomfort and practical problems in connection with the use of earplugs.

The insertion of the ear plug can involve a practical problem to many people. Typically, the plug is inserted into the ear canal by first compressing the plug by rolling the plug between the fingers. When the plug is to be inserted into the ear canal, for example into the left ear, the plug is held by the left hand while the external ear is drawn upwards and outwards with the right hand, and vice versa if the right ear is concerned. After being inserted, the plug is kept in place with a fingertip for a few seconds during the expansion thereof inside the ear canal. It is generally desirable for the earplug to fill approximately the outer half of the ear canal and to engage the wall of the ear canal after the expansion.

It has also been known to use an earplug insertion device having a hollow cylinder, which is completely open at one end thereof, with a piston displaceable in the cylinder, which has a piston rod projecting from the other end of the cylinder. Such a device has been used for insertion and orientation of an earplug by forcing the plug received in the cylinder through the open end and into the ear canal, with the open end engaged to the mouth of the ear canal.

SUMMARY

The present inventor recognized shortcomings of prior ways of inserting earplugs. For example, earplugs are often used in dirty environments, such as in many environments where industrial machinery is running. Sometimes earplugs are inserted in the user's ear canals before entering such environments. However, sometimes it is desirable for a user to insert earplugs while in these environments. For example, a user's earplugs may become dislodged while in the environment, or the user may want to remove an earplug momentarily to speak to another person. It would then be desirable to re-insert the earplugs or insert new ones before leaving the environment. However, in such environments, inserting earplugs in conventional ways can result in the earplugs becoming soiled with oil, grease, dirt or other contaminants from the air, or from a user's hands. The earplugs can then transport such contaminants into a user's ear canals, resulting in discomfort or infections in the ear canals. Even with prior cylindrical earplug insertion devices, only a single earplug was held in the device at a time. Thus, after a first earplug was inserted one ear canal, a user would handle a second exposed earplug to place the second earplug into the insertion device before the insertion device was used to insert the second earplug in the user's other ear canal. Accordingly, the second earplug could collect contaminants and transport those contaminants into the user's ear canal.

Accordingly, there existed a need to provide a new way to insert earplugs. The described embodiments address this need, which has not heretofore been recognized and addressed.

According to one embodiment, an earplug insertion device can include a housing that is configured to hold a first earplug and a second earplug. The device can also include an ejection mechanism that can be configured to respond to a first user force by ejecting the first earplug from the device in a first ejection motion. The ejection mechanism can also be configured to respond to a second user force by ejecting the second earplug from the device in a second ejection motion.

According to another embodiment, an earplug insertion casing can include a first guide holding a first earplug and a second guide holding a second earplug. The second guide can be slidably moveable relative to the first guide.

According to yet another embodiment, an earplug insertion device can hold a first earplug and a second earplug. The first earplug can be ejected from the earplug insertion device and into a first ear canal, and the second earplug can be ejected from the earplug insertion device and into a second ear canal.

This Summary is provided to introduce a selection of concepts in a simplified form. The concepts are further described below in the Detailed Description. This Summary is not intended to identify key features or essential features of the claimed subject matter, nor is it intended to be used to limit the scope of the claimed subject matter. Similarly, the invention is not limited to implementations that address the particular techniques, tools, environments, disadvantages, or advantages discussed in the Background, the Detailed Description, or the attached drawings.

BRIEF DESCRIPTION OF THE DRAWINGS

The description and drawings may refer to the same or similar features in different drawings with the same reference numbers.

DETAILED DESCRIPTION

Figure 1:
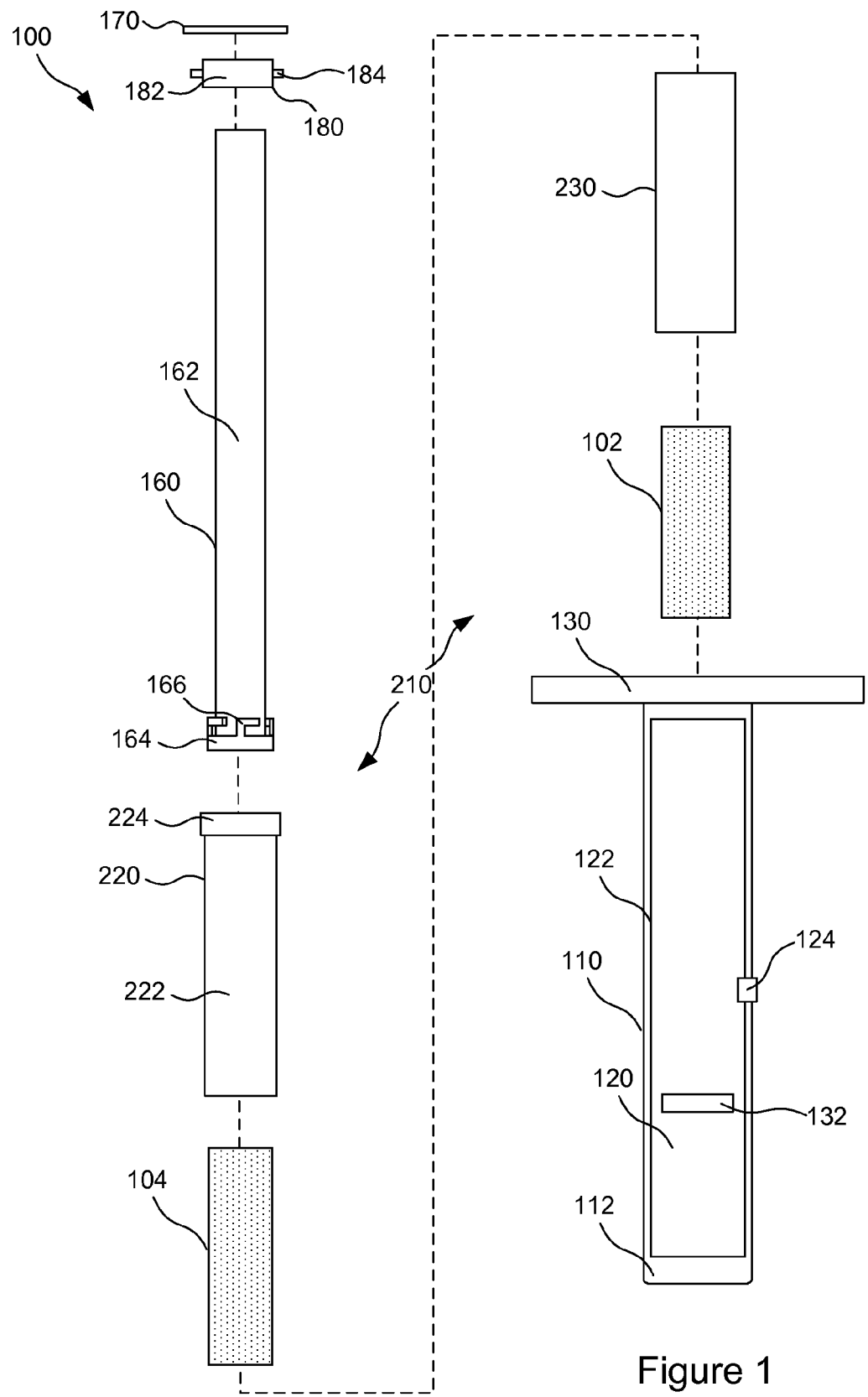
FIG. 1 is an exploded view of a described embodiment of an earplug insertion device.
Figure 2:
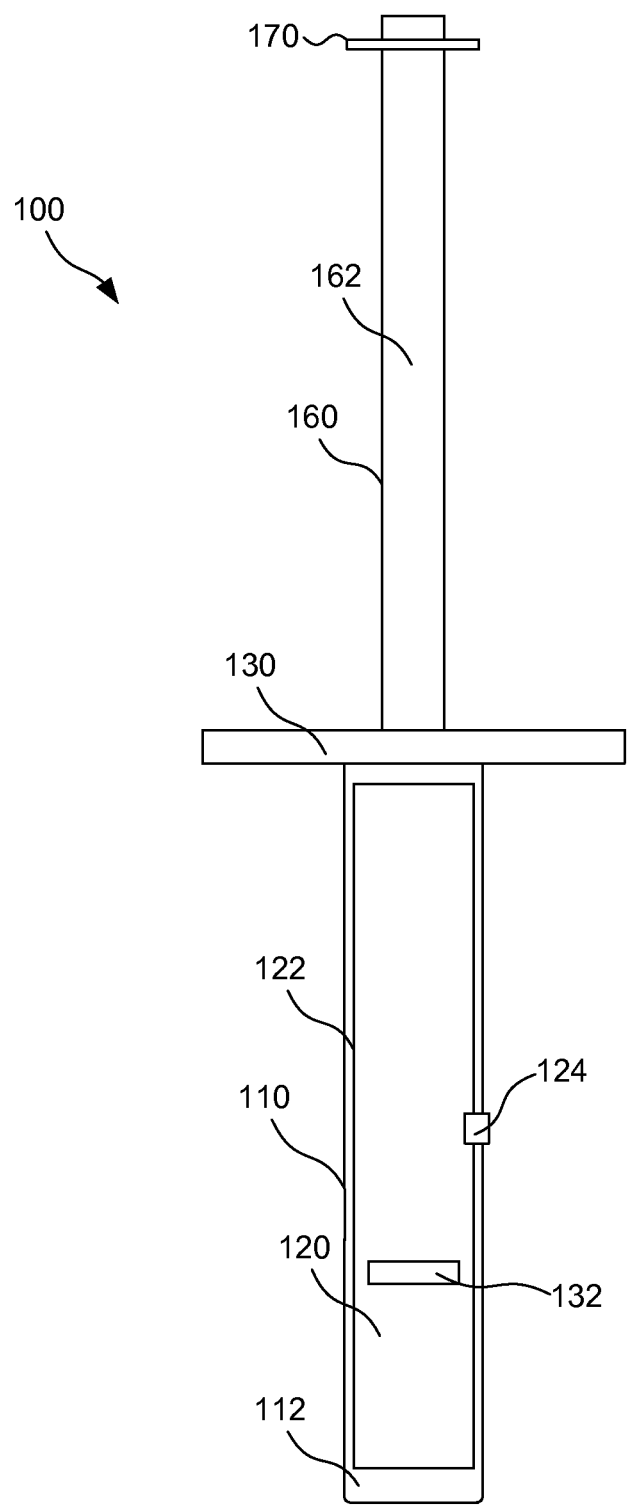
FIG. 2 is a side plan view of the earplug insertion device of FIG. 1.

An earplug insertion device (100) is illustrated in exploded form in FIG. 1, and in assembled form in FIG. 2. The device (100) can be configured to allow a user to eject a first earplug (102) and a second earplug (104) from the insertion device (100) and into a user's ear canals. Because two earplugs (102 and 104) can be housed in the device (100) at one time, and both can be ejected without fully exposing the earplugs (102 and 104) to the environment or handling the earplugs (102 and 104) with a user's hands, the earplugs (102 and 104) can be safely inserted even in dirty environments. In addition, one or more earplugs can be packaged in a casing, and the casing can be placed in the device (100) (and form a part of the device (100)). Thus, the insertion device (100) can be easily reloaded with one or more earplugs without fully exposing the earplugs to the environment or handling the earplugs directly with a user's hands. Accordingly, the illustrated embodiment can overcome drawbacks with prior earplug insertion devices and methods, which generally required exposure and handling of earplugs to insert the earplugs in a user's ears.

Figure 3:
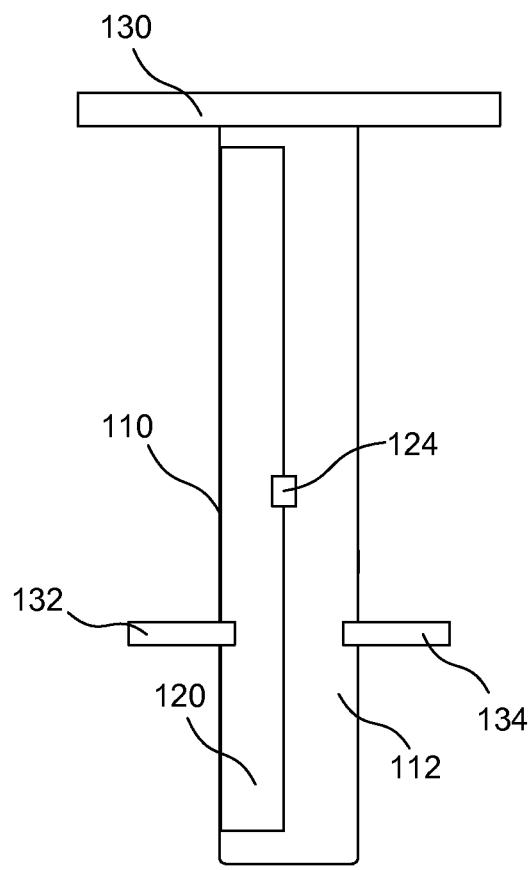
FIG. 3 is a top plan view of the housing of the earplug insertion device of FIG. 1.

Referring to FIGS. 1-3, the device (100) can include a housing (110), which can include a generally hollow cylindrical body (112) with a substantially semi-cylindrical door (120). The door (120) can run most of the length of the cylindrical body (112) and can pivot laterally about a hinge (122) to open and close (shown in open position in FIGS. 6-7). The door (120) can be releasably secured to the body (112) with a door latch (124) located opposite the hinge (122). For example, the door latch (124) can include a simple hook or protrusion extending in from the door (120) to engage a mating aperture in the cylindrical body (112). The housing (110) can also include a finger support flange (130) extending radially out from a rear end of the housing (110). The housing (110) can also include a pair of stop flanges (132 and 134) with one stop flange (132) extending out from the door (120) and another stop flange (134) extending out from the cylindrical body (112) opposite the door (120) (see FIG. 3).

Referring to FIGS. 8-11, a front of the cylindrical body (112) extends inwardly to form a front stop ring (140) and the inner edge of the front stop ring (140) defines an exit opening (142). Opposite the exit opening (142), the body (112) extends inward to form a rear stop ring (150), and an inner edge of the rear stop ring (150) defines a plunger opening (152). The body (112) can also define a pair of slots (156) that extend axially forward along opposite sides of the body (112) from a location near the rear of the body (112). The slots (156) can be located just to the side of the opening for the door (120).

Referring to FIGS. 1-2 and 8-11, the earplug insertion device (100) can also include a plunger (160) that includes a cylindrical shaft (162). A ring-shaped flange (164) can extend radially out from a front end of the cylindrical shaft (162). The plunger (160) can also include a set of fingers (166), with each finger extending axially rearward from the circular flange (164) and then circumferentially about the cylindrical shaft (162). A plunger stop ring (170) can be fixed to the cylindrical shaft (162) near a rear end of the shaft (162) and extend radially outward from the shaft (162). The plunger stop ring (170) can be fixed to the cylindrical shaft with an adhesive, with spring pressure (e.g., a lock ring), or in some other manner. As with the other parts of the device (100), the plunger could have other shapes. For example, it could have a cross-shaped cross section, a square cross section, or some other cross-sectional shape.

Figure 4:
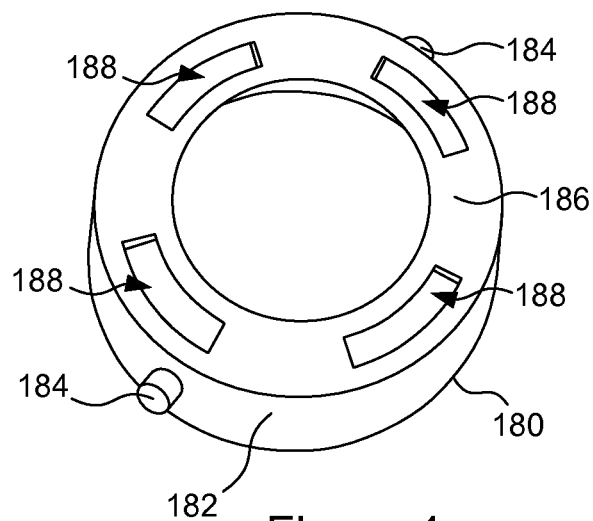
FIG. 4 is a rear perspective view of the plunger lock of the earplug insertion device of FIG. 1.
Figure 5:
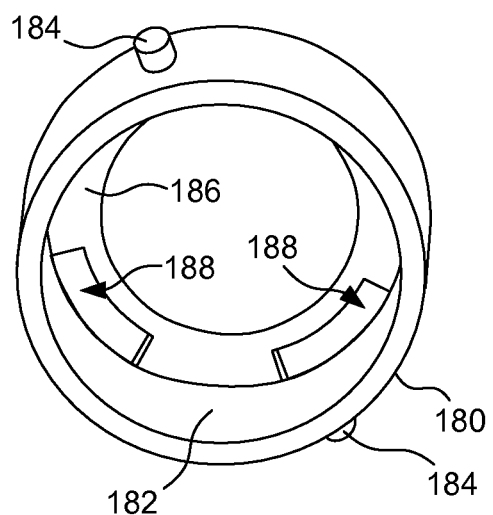
FIG. 5 is a front perspective view of the plunger lock of FIG. 4.

The device (100) can also include a plunger lock (180), which is illustrated in FIGS. 4-5, in addition to FIGS. 1 and 6-11. The plunger lock (180) can include a hollow cylindrical body (182) seated within the body (112) of the housing (110). A pair of knobs (184) can extend radially out from opposite sides of the body (182) and slide along the slots (156) in the body (112) of the housing (110). The plunger lock (180) can also include a ring-shaped flange (186) extending radially in from the rear of the cylindrical body (182). The flange (186) can define circumferentially-spaced finger holes (188) therethrough. The device (100) is shown with four fingers (166)

and four mating finger holes (188), but there could be different numbers of fingers and different numbers of finger holes.

Figure 7:
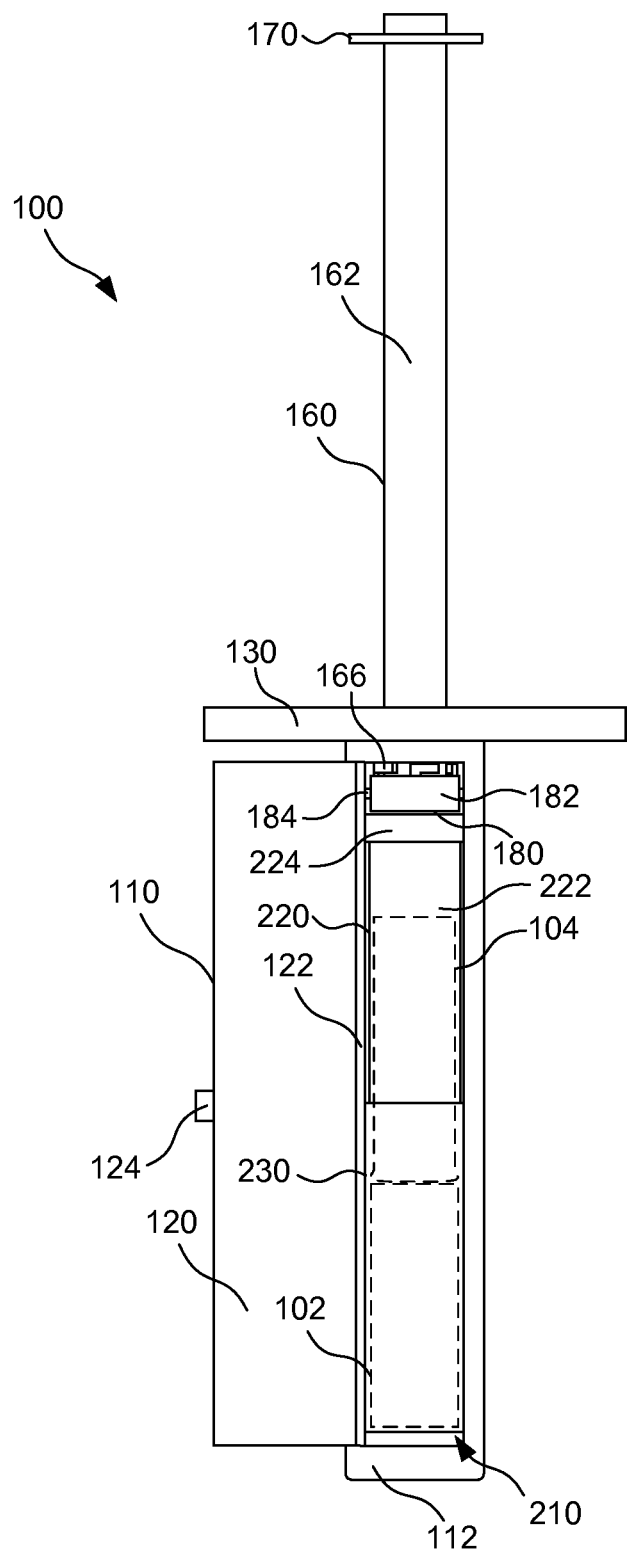
FIG. 7 is a side perspective view of the earplug insertion device of FIG. 1, similar to FIG. 6, but with the casing having been inserted in the housing.
Figure 8:
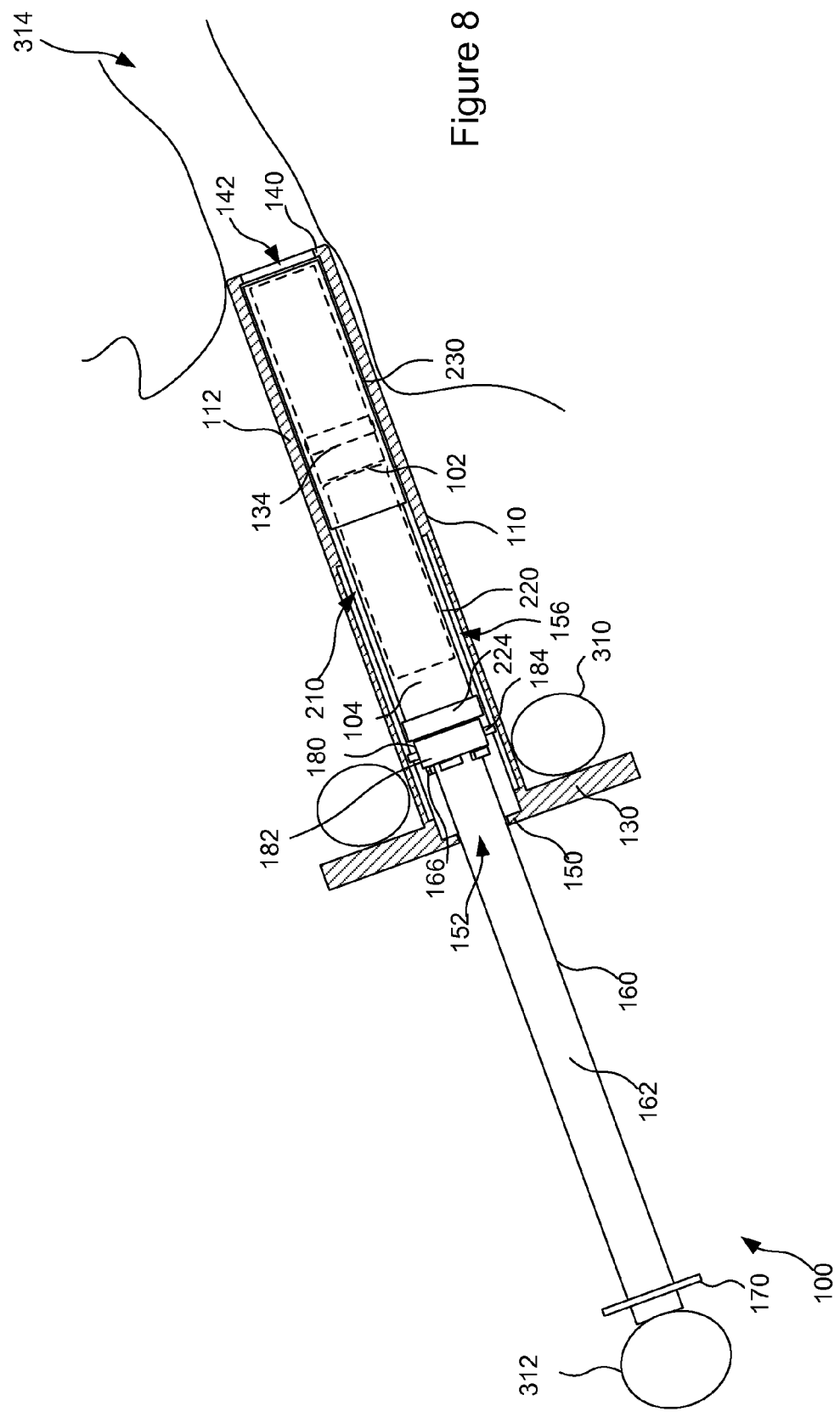
FIG. 8 is a side partially sectional view of the earplug insertion device of FIG. 1, with the insertion device loaded with earplugs and inserted in a first ear canal.

When the insertion device (100) is fully loaded with a pair of earplugs (102, 104), as illustrated in FIGS. 2, 7, and 8, the plunger lock (180) can be seated within the rear of the body (112) of the housing (110). An outside diameter of the plunger lock (180) can be less than an inside diameter of the body (112) so that the plunger lock (180) can slide axially within the body (112). The knobs (184) of the plunger lock (180) can extend into the axially-extending slots (156) in the housing. Thus, the knobs (184) can allow the plunger lock (180) to move axially along the slots (156), but prevent the plunger lock (180) from rotating relative to the housing body (112) of the housing (110). This motion could be allowed in some other manner, such as by having axially-extending rails along the sides of the body (112) correspond to slots in the plunger lock (180) or in the plunger itself (e.g., in an embodiment where the plunger lock and the removable casing could be omitted).

The circular flange (164) of the plunger (160) can be positioned within the cylindrical body (182) of the plunger lock (180) with the cylindrical shaft (162) of the plunger (160) extending back through a hole defined by the ring-shaped flange (186) in the plunger lock (180). The fingers (166) of the plunger (160) can extend back through the finger holes (188) in the plunger lock flange (186), and can extend circumferentially to engage the plunger lock flange (186). Thus, in this position, the plunger (160) and the plunger lock (180) can be secured together so that they move together in forward and rear axial directions.

The plunger (160) can be rotated relative to the plunger lock (180) so that the circumferentially-extending portions of the fingers (166) align with the finger holes (188). In that position, the plunger (160) can move axially independent of the plunger lock.

Referring now to FIGS. 1 and 6-11, the device can also include a removable casing (210). The casing (210) can include a plunger/guide (220) that includes a hollow cylindrical body (222) and a stop flange (224) extending radially out from a rear end of the cylindrical body (222). An outer diameter of the stop flange (224) of the plunger/guide (220) can be smaller than the inner diameter of the body (112) of the housing (110) so that the plunger/guide can slide axially within the body (112). The casing (210) can also include a guide (230) that can be a hollow cylinder with an outer diameter slightly smaller than the inner diameter of the body (112) of the housing (110) but larger than the inner diameter of the front stop ring (140) of the housing (110). An inner diameter of the guide (230) can be slightly larger than an outer diameter of the cylindrical body (222) of the plunger/guide (220), but smaller than an outer diameter of the stop flange (224) of the plunger/guide (220). Thus, the guide (230) can fit within the housing body (112) but cannot slide forward of the front stop ring (140) of the housing (110). In addition, the body of the plunger/guide (220) can slide within the guide (230), but that sliding motion is stopped when the stop flange (224) at the rear of the plunger/guide (220) contacts a rear end of the guide (230).

When the device (100) is fully loaded, the casing (210) can hold the earplugs (102 and 104). More specifically, the first earplug (102) can be seated in a front portion of the guide (230) and a front portion of the plunger/guide (220) can be seated within a rear portion of the guide (230). The second earplug can be seated in a front portion of the plunger/guide (220). The casing (210) can be seated within the housing body (112) with the front of the guide (230) abutting the front stop ring (140), and with the rear of the plunger/guide (220) abutting the plunger lock (180).

The parts of the device (100) can be made from any of a variety of materials, so long as the materials are sufficiently rigid and durable. However, it may be desirable to have some parts be somewhat flexible. For example, it may be desirable for the portion of the housing (110) that will extend into the ear canal be somewhat flexible, such as by being formed off an elastomeric material. In addition, all the parts may be made from the same material, or some parts may be made from different materials than others. For example, the parts of the device (100) could be made of the material sold under the name Teflon by DuPont, polypropylene, polystyrene, polyvinyl chloride (PVC), and/or Polyurethanes. Other possible materials include high density polyethylene, polyethylene terephthalate, or other polymer materials, or even other types of materials, such as composites or metals.

A variety of different manufacturing processes could be used to form and assemble the parts of the device (100). For example, the housing (110), plunger (160), plunger stop ring (170), plunger lock (180), plunger/guide (220), and guide (230) can all be formed by injection molding. Alternatively, one or more of the parts can be formed by extrusion, possibly in combination with other methods, such as adhering various parts to an extruded cylindrical body. For example, the guide (230) can be formed by extrusion. The plunger/guide (220) could also be formed by extrusion, with the stop flange (224) being adhered to the extruded cylindrical body (222).

In assembly, the cylindrical shaft (162) of the plunger (160) can be placed through the plunger lock (180). The plunger stop ring (170) can be placed on the cylindrical shaft (162), such as by adhering, or by mechanical pressure if the stop ring (170) is a lock ring (such as a metal lock ring that fits in a corresponding annular groove in the cylindrical shaft (not shown)). The plunger lock (180) can be seated in the body (112) of the housing (110). This may include temporarily deforming the housing (110) by squeezing the rear of the housing (110) to separate the axially-extending slots (156) and allow the knobs (184) of the plunger lock (180) to enter the slots (156) of the housing (110). The plunger (160) can be locked to the plunger lock (180) by rotating the plunger (160) to align the fingers (166) with the finger holes (188); pulling plunger (160) rearward so that the fingers (166) extend through the finger holes (188); and rotating the plunger (160) in the direction that the finger ends are pointing so that the fingers (166) of the plunger engage the ring-shaped flange (186) of the plunger lock (180).

Figure 6:
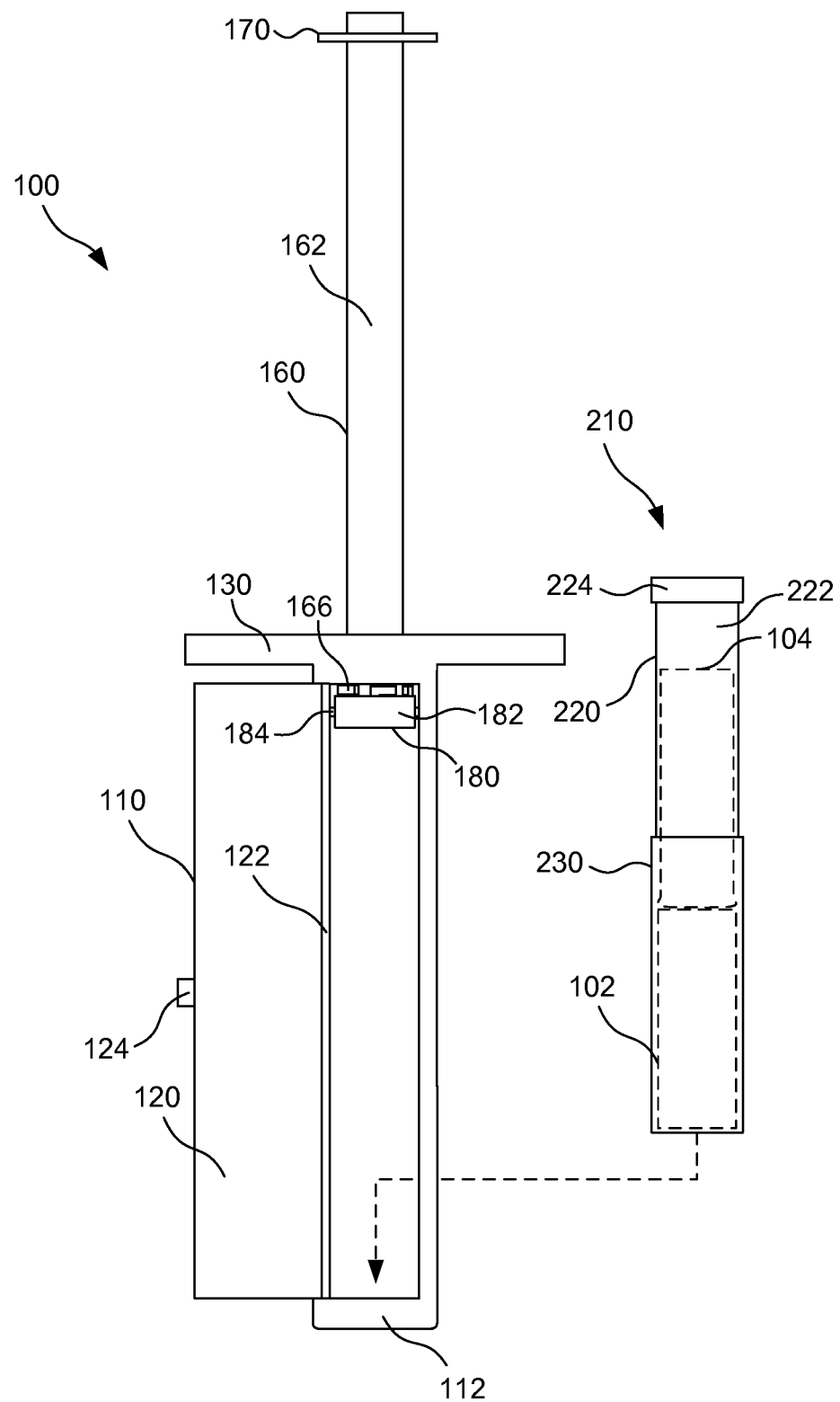
FIG. 6 is a side perspective view of the earplug insertion device of FIG. 1, illustrating insertion of a casing in the housing.

The casing (210) can be loaded by placing the second earplug (104) in the plunger/guide (220). This can be done manually by pressing on or rolling the second earplug (104) with a person's fingers to reduce the earplug's diameter, and then placing the second earplug (104) in the plunger/guide (220). The earplug (104) can protrude slightly forward from the plunger/guide (220) to keep the first earplug (102) from sliding back into the plunger/guide (220) when the plunger/guide (220) is plunging the first earplug (102) from the guide (230), as discussed below. Alternatively, a plunger could be used to push the second earplug (104) through a funnel-shaped loader and into the plunger/guide (220). The first earplug (102) can be placed in the guide (230) in the same manner as the second earplug (104) is placed in the plunger/guide (220), but the first earplug (102) can be located entirely within the guide (230). The front of the plunger/guide (220) can be slid into the rear of the guide (230) to form the casing (210), as illustrated in FIG. 6. This loading of earplugs (102 and 104) in the casing (210), and possibly packaging of the removable casing (210), can be done in an environment that is relatively clean. It may also be desirable to minimize humidity in the environment. A similar type of environment may be useful when loading earplugs in the other devices described below.

Referring still to FIG. 6, to place the removable casing (210) in the body (112) of the housing (110), the door (120) of the housing (110) can be opened. The plunger lock (180) and the front of the plunger (160) can be slid rearward until the plunger lock knobs (184) abut the rear of the axially-extending slots (156), as illustrated in FIG. 6. The casing (210) can then be placed in the body (112) through the door opening, as illustrated in FIGS. 6-7. The door (120) can then be closed.

Alternatively, the body (112) could be a hollow cylindrical body without a door; the rear stop ring (150) could be omitted; and the slots (156) could extend all the way to the rear of the housing body (112). In such an embodiment, the plunger (160) and plunger lock (180) could be removed by pulling them from the rear of the housing body (112). The casing (210) could then be inserted in the rear of the housing body (112), and the plunger (160) and plunger lock (180) could then be re-inserted in the rear of the housing body (112). As another alternative, the housing body (112) could define an opening where the door (120) is illustrated, without having a door to cover the opening.

Referring now to FIG. 8, use of the device (100) will be described. As illustrated in FIG. 8, the device (100) can be grasped with two of a user's fingers (310), such as the index and middle fingers, with the fingers against a forward side of the rear stop ring (150) on opposite sides of the body (112). The user's thumb (312) on the same hand can rest against the rear of the plunger (160). The portion of the housing (110) that is forward of the stop flanges (132 and 134) can be slid into a user's first ear canal (314). As illustrated in FIG. 8, the stop flanges (132 and 134) can keep the housing (110) from being inserted too far into the first ear canal (314), though a user may be able to determine the correct depth of the device without such flanges. The outside diameter of the housing body (112) can be small enough to fit comfortably within the user's first ear canal (314), as illustrated.

Figure 9:
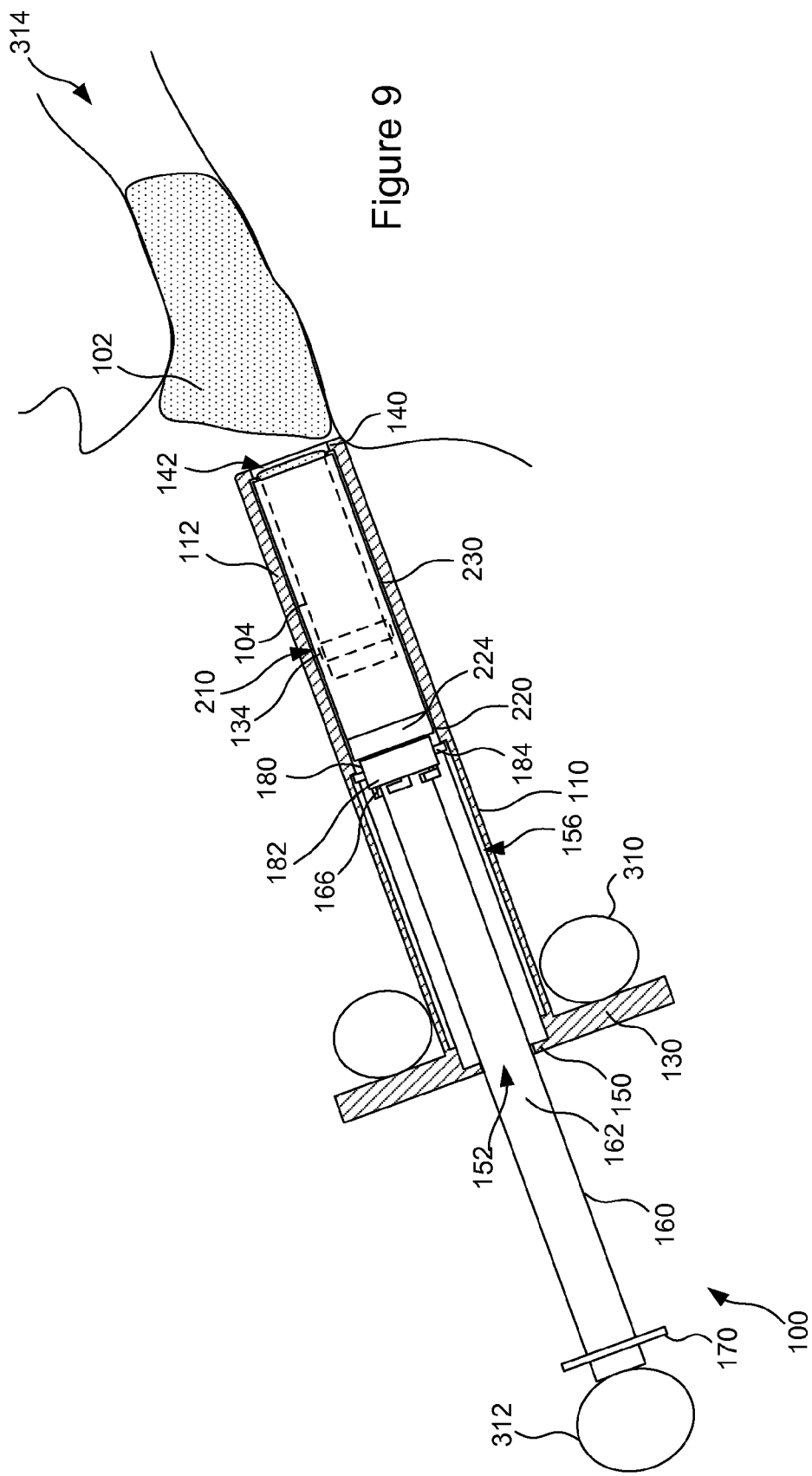
FIG. 9 is a side partially sectional view similar to FIG. 8, after a first earplug has been ejected from the device into the first ear canal.

To eject the first earplug (102) into the first ear canal (314), the user can move the thumb (312) forward and pull the housing (110) rearward with the user's fingers (310). These two parts of this motion can be done sequentially (e.g., move the thumb forward and then pull the fingers rearward), simultaneously, or with some combination of simultaneous and sequential movement. During this motion, the housing (110) can pull the guide (230) rearward. However, the plunger (160) and the plunger lock (180) are secured together by the fingers (166) so that the plunger lock keeps the plunger/guide (220) from being pulled rearward and moves the plunger/guide (220) forward. The plunger/guide (220) in turn keeps the first earplug (102) from being pulled rearward, and moves the first earplug (102) forward into the ear canal (314). Accordingly, the guide (230) slides over the plunger/guide (220), and the plunger/guide (220) plunges the first earplug (102) out of the device (100), leaving the earplug properly placed in the user's first ear canal (314), as illustrated in FIG. 9. The plunger lock (180) stops axial movement when the lock (180) reaches the front end of the axially-extending slots (156) in the housing (110), thereby inhibiting further movement of the plunger (160) to keep a user from inadvertently ejecting both earplugs (102 and 104) at once.

Figure 10:
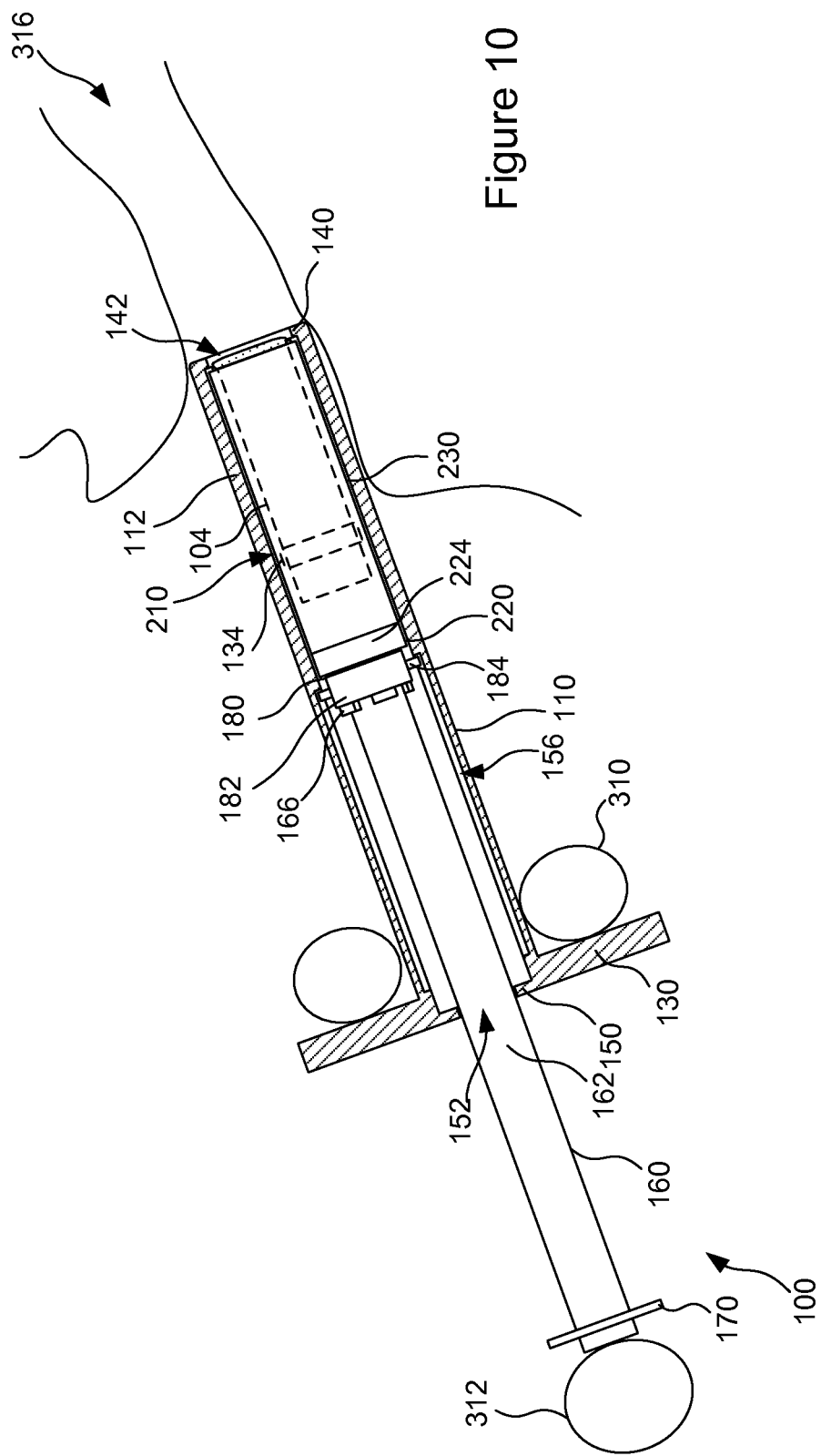
FIG. 10 is a side partially sectional view similar to FIG. 8, but with the earplug insertion device loaded with only a second earplug and inserted in a second ear canal (which could be the same ear canal as the first ear canal, but at a later time, as used with reference to this and other embodiments).
Figure 11:
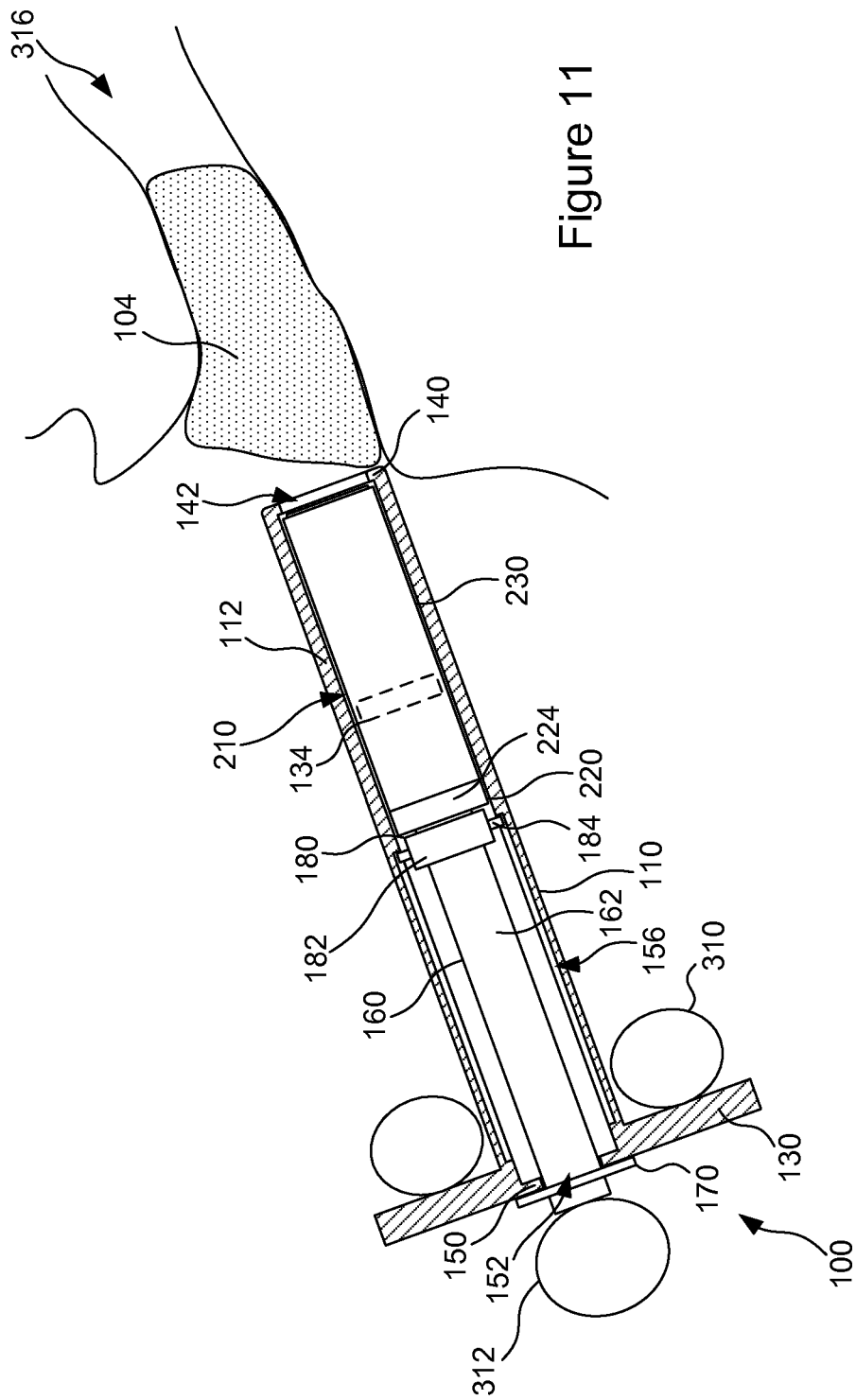
FIG. 11 is a side partially sectional view similar to FIG. 10, after the second earplug has been ejected from the earplug insertion device into the second ear canal.
Figure 12:
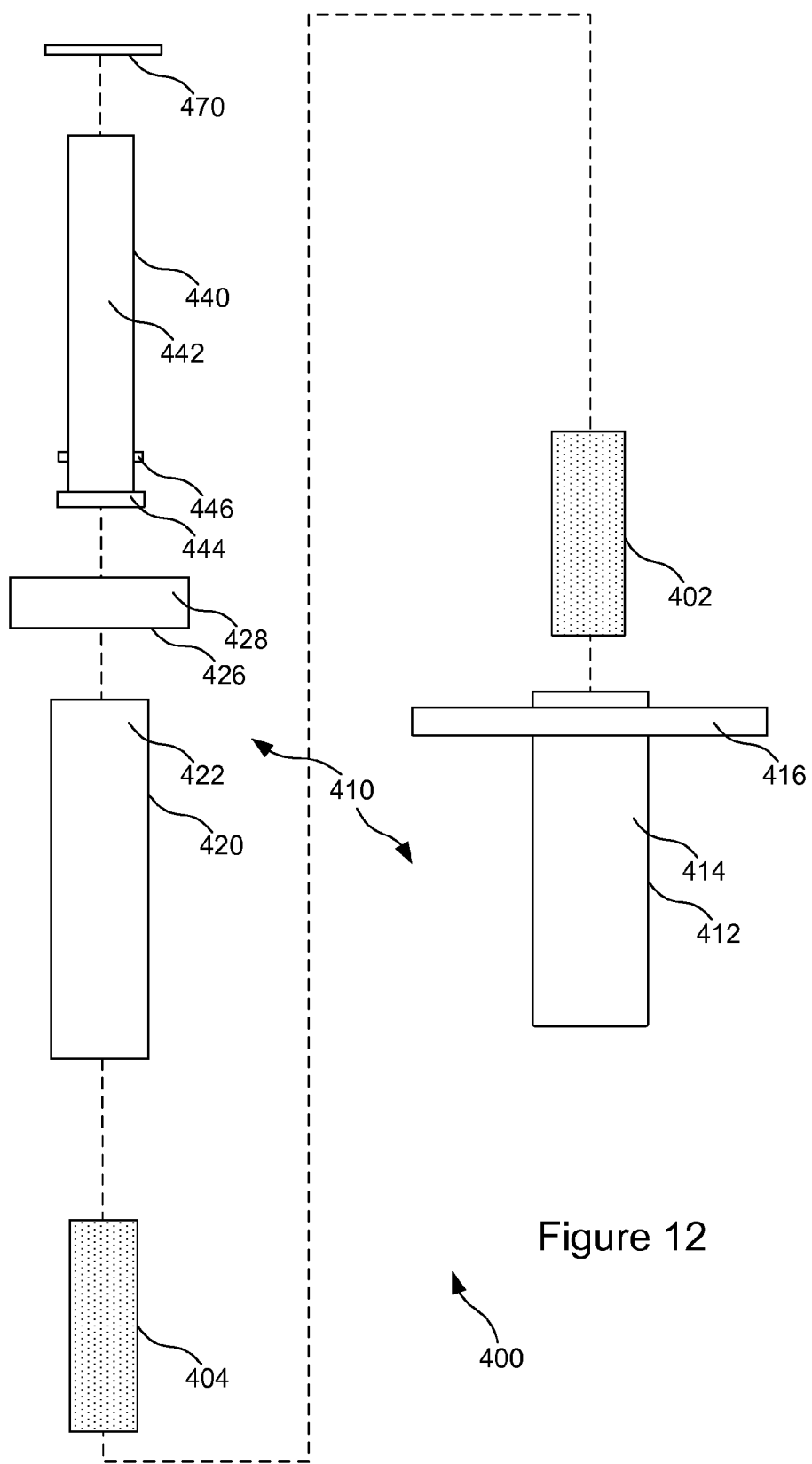
FIG. 12 is an exploded view of another described embodiment of an earplug insertion device.

To eject the second earplug (104), the plunger (160) can be rotated in a direction opposite from the direction the ends of the fingers (166) are pointing so that the fingers (166) align with the finger holes (188). The plunger (160) can then move axially independent of the plunger lock (180). Referring to FIG. 10, the device (100) can be placed with the portion of the housing (110) forward of the stop flanges (132 and 134) extending into a second ear canal (316). As used herein, the second ear canal (316) can be the same ear canal as the first ear canal (314), but at a later time; a different ear canal in the same person as the first ear canal (314); or an ear canal in a different person. In contrast, for parts of the devices described below, first and second parts refer to two parts, and not to one part at two different times, though the two parts may be identical (e.g., first and second earplugs refers to two earplugs, and first and second guides described with reference to FIGS. 27-35 refers to two guides). The user's fingers (310) can pull back on the housing (110) and the user's thumb (312) can move the plunger (160) forward. The housing (110) can pull the guide (230) and the plunger lock (180) rearward. The guide (230) can also abut the stop flange (224) of the plunger/guide (220) to pull the plunger/guide (220) back with the housing (110). However, the plunger (160) can move forward, sliding within the plunger/guide (220) to eject the second earplug (104) from the device (100) and into the second ear canal (316) in a manner similar to the ejection of the first earplug (102) discussed above, as illustrated in FIG. 11. The plunger stop ring (170) can inhibit further movement of the plunger (160) relative to the housing (110) to keep the plunger (160) together with the remainder of the device (100) and to prevent the front of the plunger (160) from extending out of the housing (110) during use.

Accordingly, the ejection mechanism of the device (100), which responds to a user force by ejecting the earplugs (102 and 104), can include all the parts of the device (100), including the housing (110). The same is generally true of the other specific embodiments described below. However, in some embodiments, an ear insertion device could include additional parts that are not part of the ejection mechanism.

Both ejections can be accomplished without fully exposing the earplugs (102 and 104) to the environment and without a user needing to touch either earplug. Indeed, if a user had multiple removable casings (210) loaded with earplugs (102 and 104), the user could insert earplugs as many times as necessary (so long as the user had enough loaded casings (210)) without touching any of the earplugs. Accordingly, the insertion operation and/or device described herein can make the insertion of earplugs easier and safer in any environment, but especially in dirty environments.

Referring to FIGS. 12-19, an alternative earplug insertion device (400) for inserting a first earplug (402) and a second earplug (404) is illustrated. The insertion device (400) can include a housing (410), which can include a guide (412). The guide (412) can include a hollow cylindrical body (414) and a circular flange (416) extending radially out from the body (414) near a rear end of the body (414). The guide (412) can define an exit opening (418) through which both the earplugs (402 and 404) can exit the device (400) (see FIGS. 16-19). The body (414) can hold the first earplug (402) when the device (400) is loaded with earplugs (402 and 404). The housing (410) can also include a plunger/guide (420) that can have a cylindrical body (422), which can be long enough so that the plunger/guide (420) can hold the second earplug (404). The outside diameter of the cylindrical body (422) of the plunger/guide (420) can be smaller than the inside diameter of the cylindrical body (414) of the guide (412), so that the plunger/guide (420) can slide axially within the guide (412). The housing (410) can also include a cap (426) on the plunger/guide (420). The cap (426) can include a generally cylindrical body (428) that defines a large diameter hole (430) extending back from a front side of the cap (426), and a small diameter hole (432) that extends further back and through the back side of the cylindrical body (428). A pair of slots (434) can extend along opposite sides of the small diameter hole (432).

The device (100) can also include a plunger (440), which can include a cylindrical shaft (442), which can be sized to easily slide within the small diameter hole (432). The plunger (440) can also include a circular flange (444) extending out from a front of the cylindrical shaft (442). In addition, the plunger (440) can include a pair of knobs (446) positioned near a front of the shaft (442) but rearward of the circular flange (444). The knobs (446) can extend out from opposite sides of the cylindrical shaft (442). A plunger stop ring (470) can also be secured to the plunger shaft (442), such as with spring compression or an adhesive.

When the device (400) is loaded with earplugs (402 and 404), the first earplug (402) can be held in a front portion of the body (414) of the guide (412). The large diameter hole (430) in the cap (426) can receive an end of the plunger/guide (420) in an interference fit so that the cap (426) is generally secured to the plunger/guide (420) during use, but can be removed when sufficient force is applied. Alternatively, the plunger/guide (420) and the cap (426) could be secured together with a threaded connection, with an adhesive, or in some other manner besides a simple interference fit. Other parts of the device (400) and the other devices described herein could also be held together with interference fits, threaded connections, adhesives, and/or other ways of securing parts together. If the plunger/guide (420) and the cap (426) are secured together with only friction from an interference fit, it may be desirable to have an outwardly-extending stop ring secured to the plunger/guide (420) adjacent to the cap (426). Such a stop ring could prevent the plunger/guide (420) from being dislodged from the cap (426) and being accidentally pushed through the guide (412) and into an ear canal, along with the earplug that it holds. A front portion of the cylindrical body (422) of the plunger/guide (420) can extend into a rear portion of the guide (412). The knobs (446) of the plunger (440) can be positioned behind the cap (426), and can be out of alignment with the slots (434) of the cap (426). The cylindrical shaft (442) of the plunger (440) can extend through the small diameter hole (432) in the cap (426), and the circular flange (444) of the plunger (440) can be positioned within the plunger/guide (420) just forward of the small diameter hole (432) in the cap (426). While the knobs (446) are out of alignment with the slots (434) (in a locked position), the plunger (440) can move together with the cap (426) and the plunger/guide (420).

The parts of the device (400) can be formed from materials and by manufacturing and assembly processes similar to those described above with reference to the device (100). The device (400) can be loaded with earplugs (402 and 404) by inserting the first earplug (402) in the guide (412) in a manner similar to inserting the first earplug (102) in the guide (230), described above. Similarly, the second earplug (404) can be inserted in the plunger/guide (420) in a manner similar to inserting the second earplug (104) in the plunger/guide (220) described above. The earplug (404) can protrude slightly forward from the plunger/guide (420) to keep the first earplug (402) from sliding back into the plunger/guide (420) when the plunger/guide (420) is plunging the first earplug (402) from the guide (412), as discussed below. This can be done with the knobs (446) of the plunger (440) rearward of the cap (426) and out of alignment with the slots (434) of the cap (426) (in the locked position). The plunger/guide (420) can then be inserted in the rear of the guide (412) until the plunger/guide (420) abuts the first earplug (402).

Alternatively, the plunger/guide (420) and the guide (412) could be pre-loaded with the earplugs (402 and 404) and the plunger/guide (420) could be inserted in the rear of the guide (412) to form a disposable refill, or casing. A user could insert the plunger/guide (420) into the large diameter hole (430) of the cap (426) to form the insertion device (400). After the user inserts the earplugs (402 and 404), the user could dispose of the plunger/guide (420) and the guide (412), and insert a new refill (including a new plunger/guide (420) and guide (412) loaded with new earplugs (402 and 404)). This could be done without a user needing to touch either of the earplugs (402 or 404).

Figure 16:
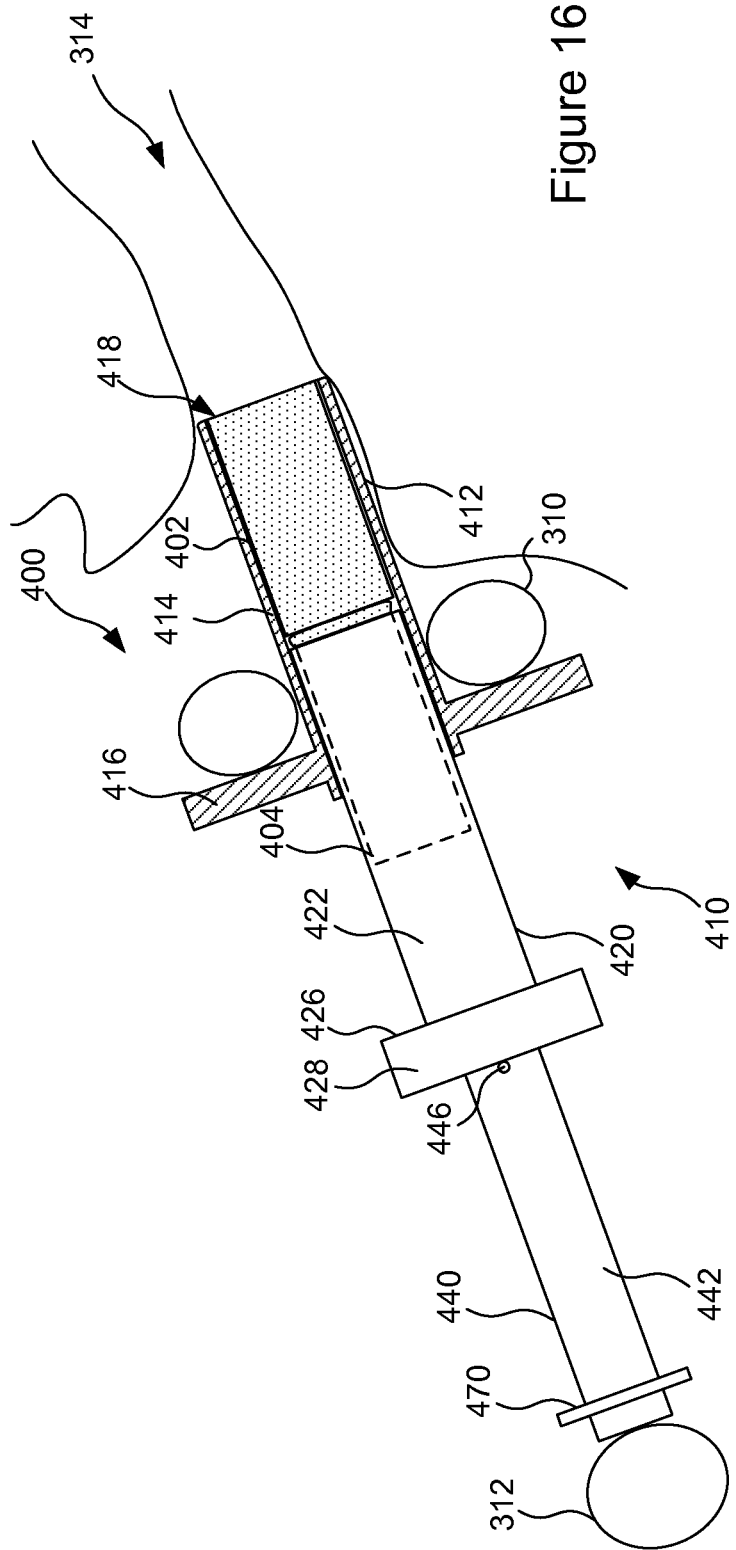
FIG. 16 is a side partially sectional view of the earplug insertion device of FIG. 12, with the device being loaded with earplugs and inserted in a first ear canal.
Figure 17:
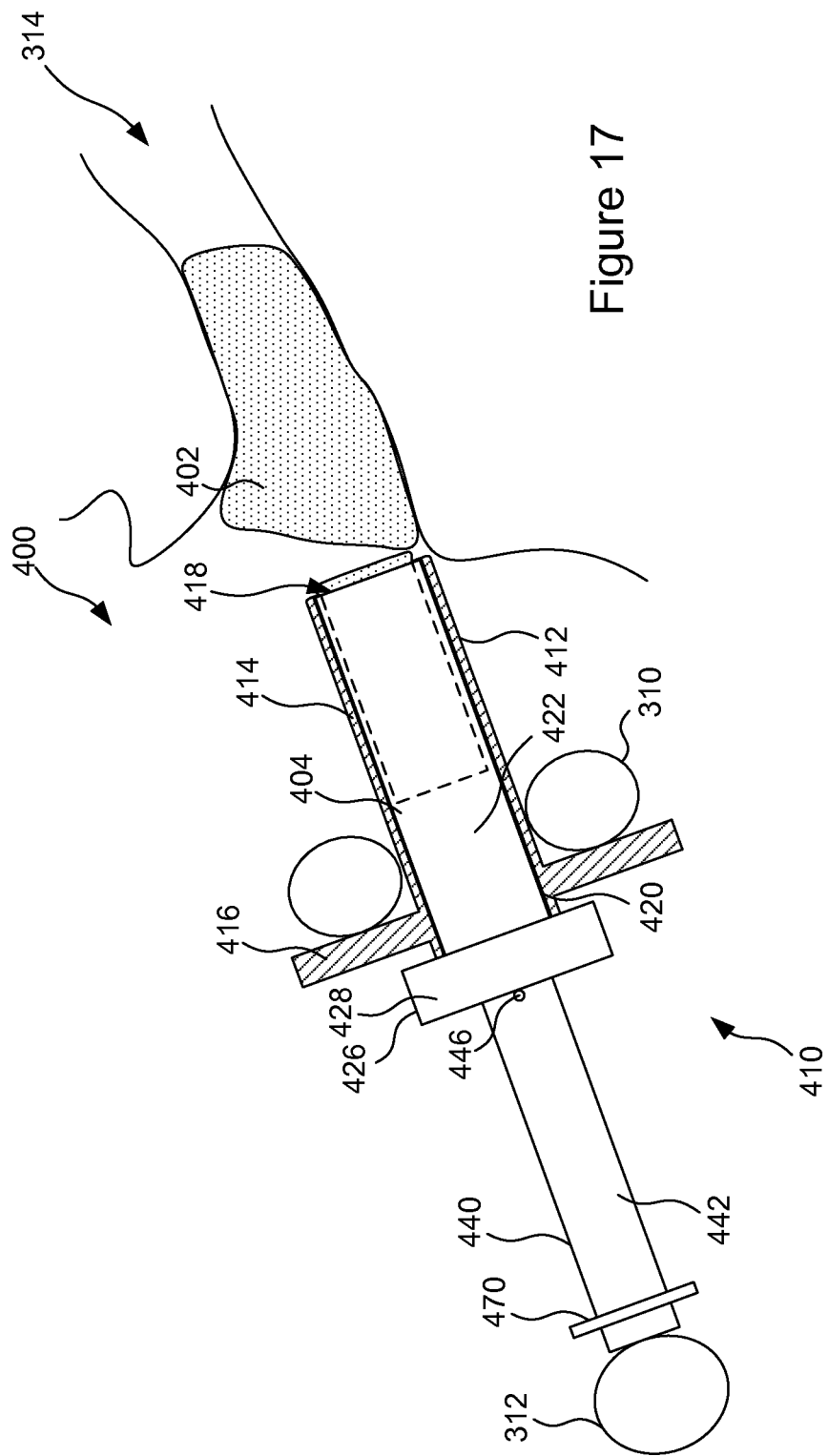
FIG. 17 is a side partially sectional view similar to FIG. 16, but after a first earplug has been ejected from the earplug insertion device into the first ear canal.

As illustrated in FIG. 16, the device (400) can be grasped with a pair of the user's fingers (310) on opposite sides of the body (414) of the guide (412) just forward of the circular flange (416), and with the user's thumb (312) on the rear of the plunger (440). The user can position the device (400) with the front of the guide (412) extending into the first ear canal (314). The user can pull the guide (412) rearward with the user's fingers (310), while moving the plunger (440) forward. Thus, the plunger/guide (420) can also move forward because the plunger/guide (420) is in the locked position with respect to the plunger (440). The plunger/guide (420) can thus plunge the first earplug (402) out of the guide (412) through the exit opening (418) and unto the first ear canal (314) as the plunger/guide (420) slides forward within the rearward-moving guide (412), as illustrated in FIG. 17. The movement of the plunger/guide (420) into the guide (412) can be inhibited when the cap (426) abuts the guide (412). Accordingly, the device (400) can inhibit further movement once the first earplug (402) is ejected. This can help prevent a user from inadvertently forcing the plunger/guide (420) and/or the earplug (402) too far into the ear canal (314).

Figure 13:
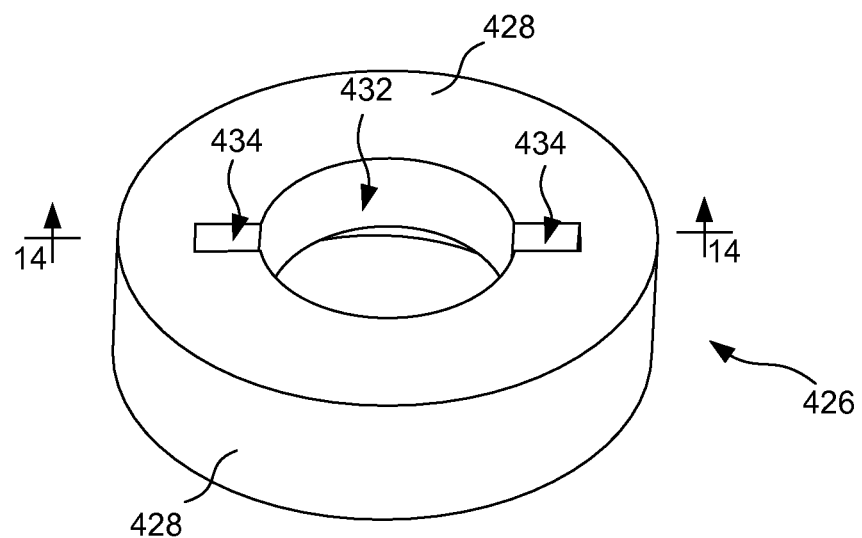
FIG. 13 is a rear perspective view of a cap of the earplug insertion device of FIG. 12.
Figure 14:
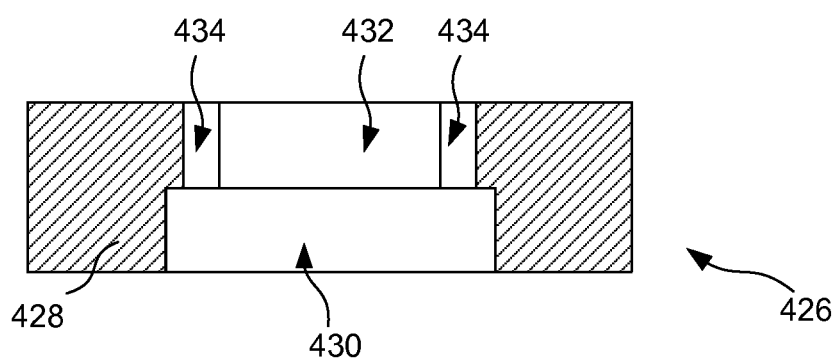
FIG. 14 is a sectional view taken along line 14-14 of FIG. 13.
Figure 15:
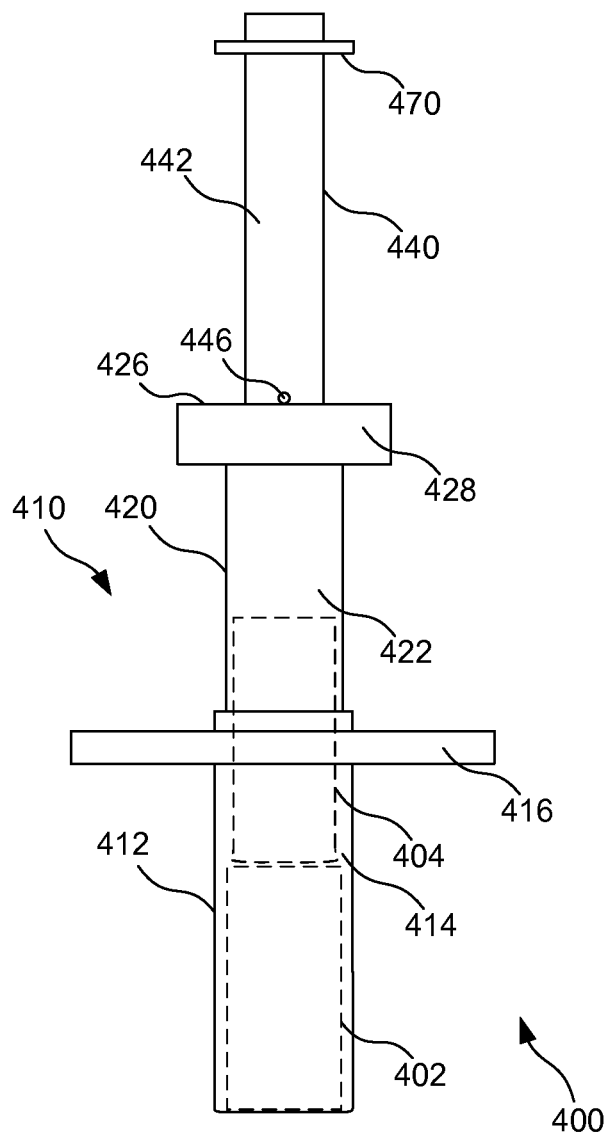
FIG. 15 is a side plan view of the earplug insertion device of FIG. 12.
Figure 18:
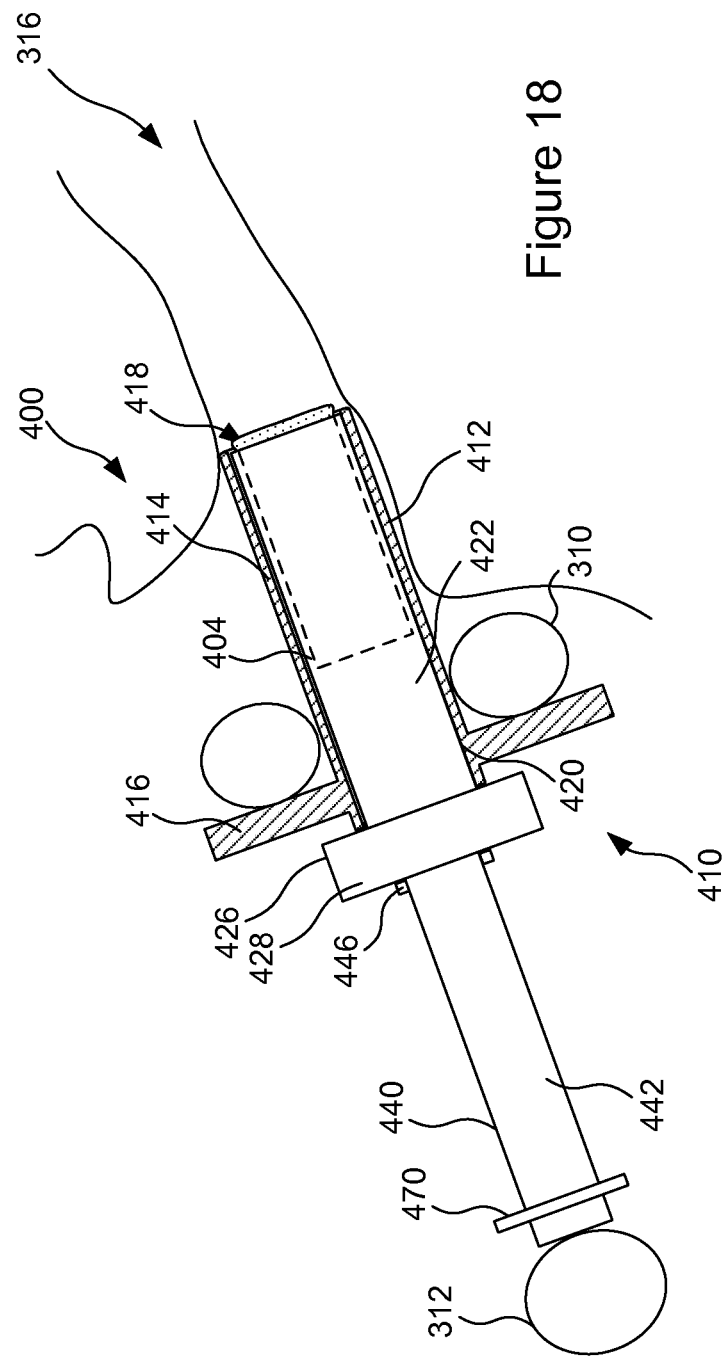
FIG. 18 is a side partially sectional view similar to FIG. 16, but with the earplug insertion device loaded only with a second earplug and inserted in a second ear canal.
Figure 19:
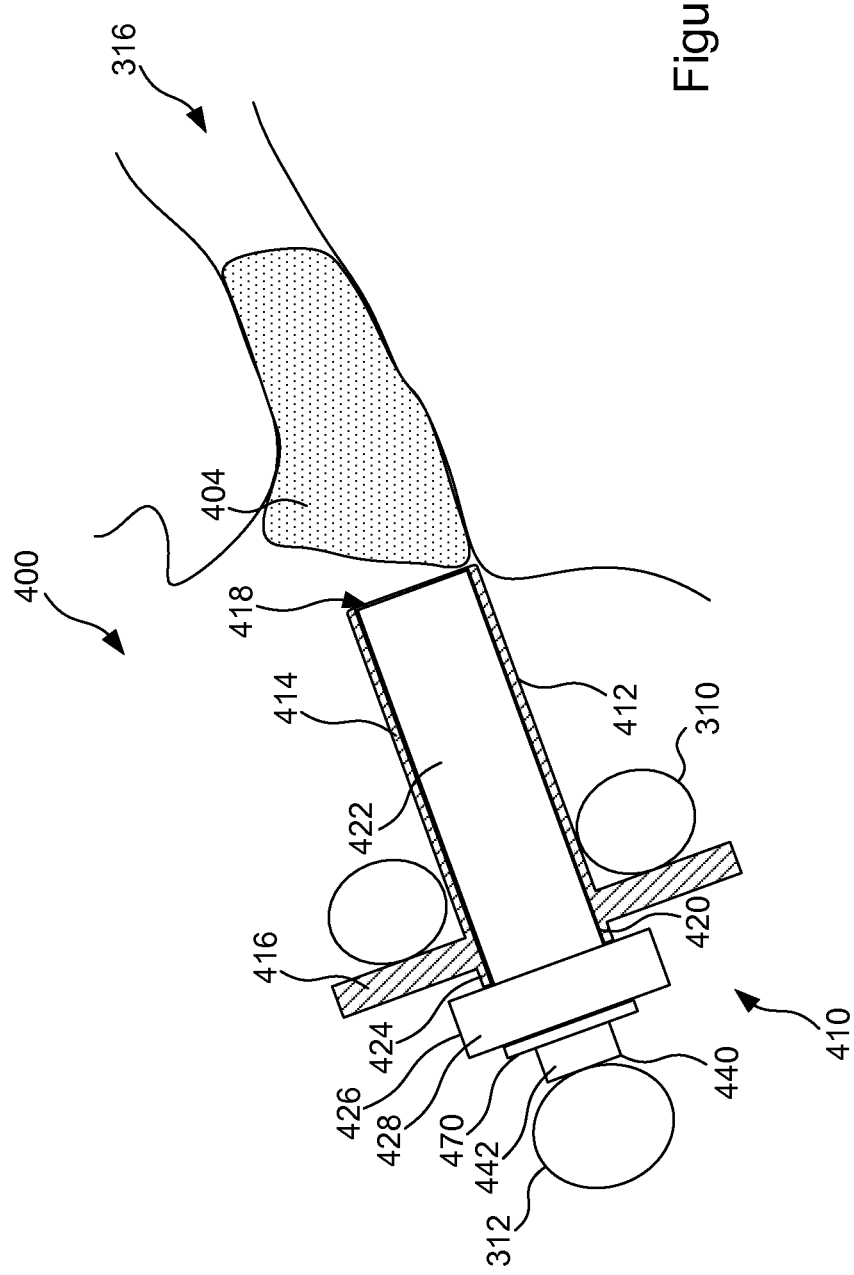
FIG. 19 is a side sectional view similar to FIG. 18, but after the second earplug has been ejected from the earplug insertion device into the second ear canal.
Figure 20:
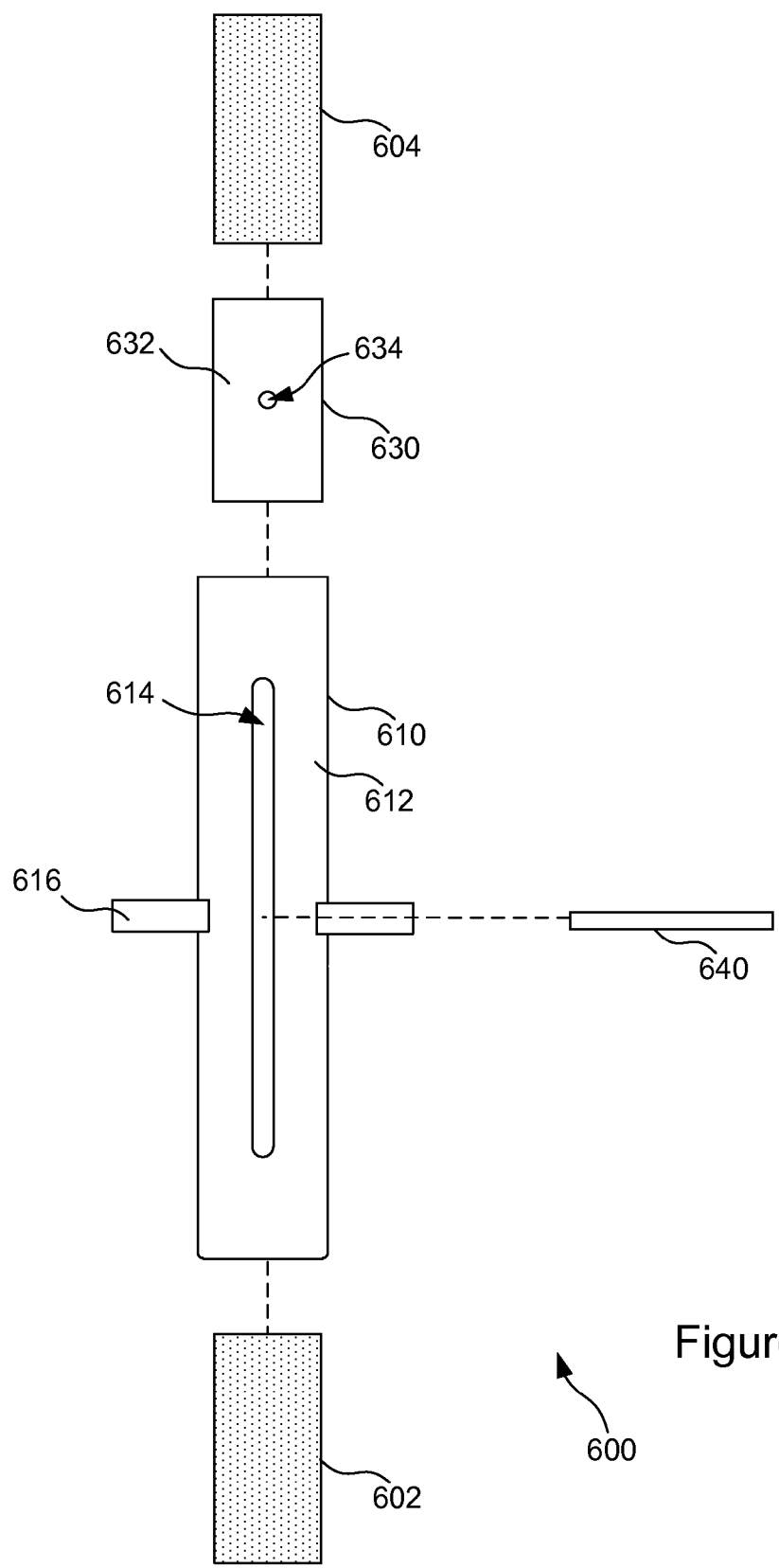
FIG. 20 is an exploded view of another described embodiment of an earplug insertion device.

Referring to FIG. 18, a user can rotate the plunger (440) relative to the cap (426) so that the knobs (446) of the plunger (440) align with the slots (434) of the cap (426) (see also FIGS. 13-14). The user can then position the device (400) with the front portion of the guide (412) extending into the second ear canal (316), as illustrated in FIG. 18. The user can pull back on the flange (416) of the guide (412) with the fingers (310), while using the thumb (312) to move the plunger (440) forward, to eject the second earplug (404). Because the cap (426), which is secured to the plunger/guide (420), abuts the guide (412), this motion can also pull the plunger/guide (420) rearward. The plunger (440) can thus slide forward into the plunger/guide (420) to plunge the second earplug (404) out of the plunger/guide (420) and into the second ear canal (316) through the exit opening (418), as illustrated in FIG. 19.

Referring to FIGS. 20-26, another earplug insertion device (600) for inserting a first earplug (602) and a second earplug (604) will be described. The device (600) can include a housing/guide (610), which can include a hollow cylindrical body (612). The body (612) can define a pair of axially-extending slots (614) that extend through a wall of the body (612) on opposite sides of the body (612). The housing/guide (610) can also include a pair of flanges (616) extending radially out from a central portion of the body (612). The flanges (616) can be circumferentially offset by about ninety degrees relative to the axially-extending slots (614). The housing/guide (610) can define exit openings (not shown) at each end through which the earplugs (602 and 604) can exit the device (600).

The device (600) can also include a plunger (630), which can include a substantially cylindrical body (632) defining a radially-extending hole (634) therein. The plunger (630) can have an outer diameter that is less than an inner diameter of the body (612) of the housing/guide (610) so that the plunger (630) can slide axially within the body (612). A rod (640) can extend through the hole (634) in the plunger (630) and through the slots (614) in the housing/guide (610).

Figure 21:
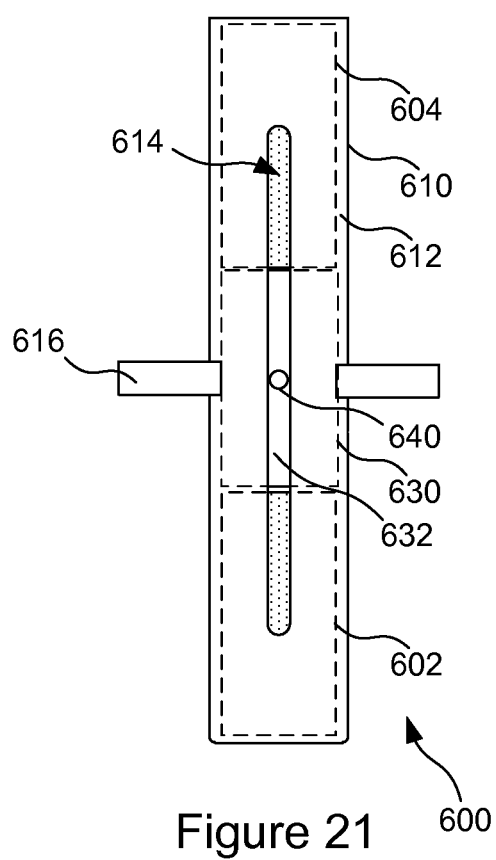
FIG. 21 is a side plan view of the earplug insertion device of FIG. 20.
Figure 22:
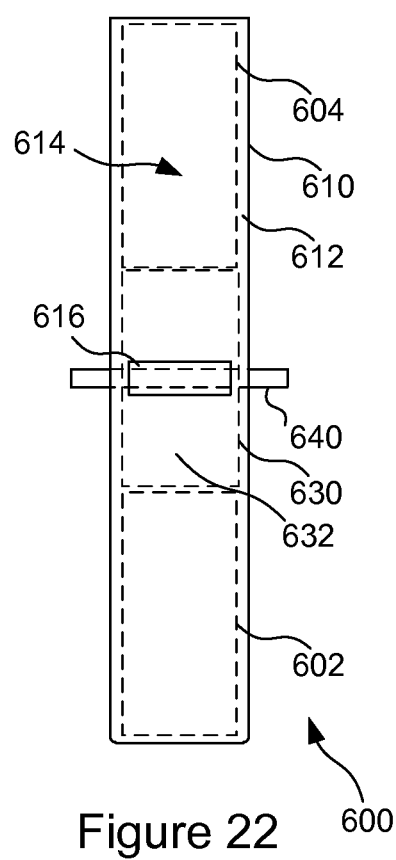
FIG. 22 is a top plan view of the earplug insertion device of FIG. 20.
Figure 23:
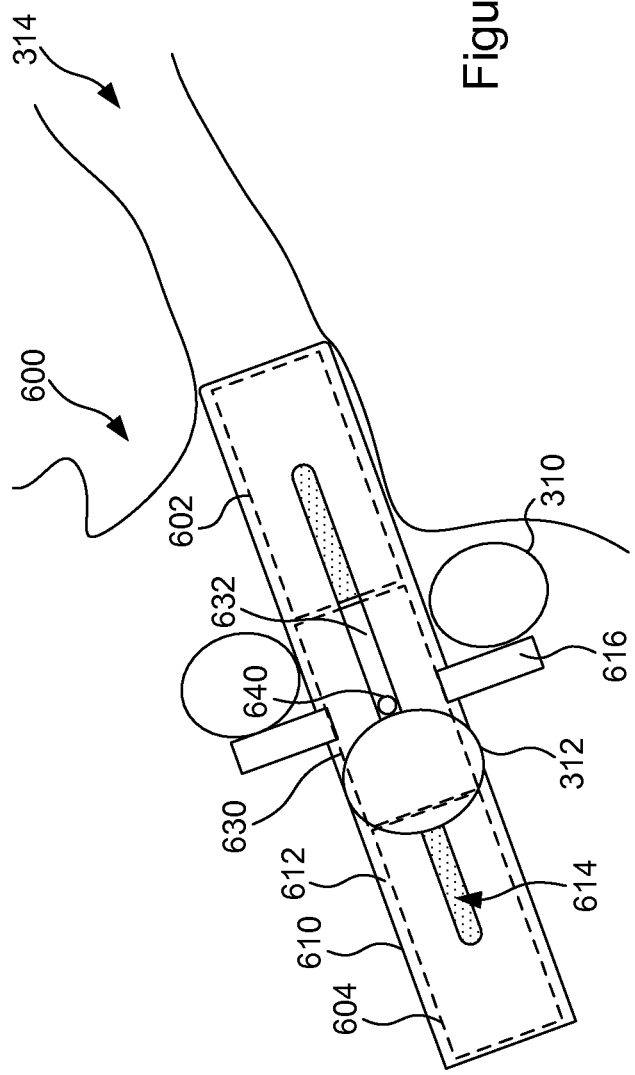
FIG. 23 is a side plan view of the earplug insertion device of FIG. 20, with the earplug insertion device being loaded with earplugs and inserted in a first ear canal.
Figure 24:
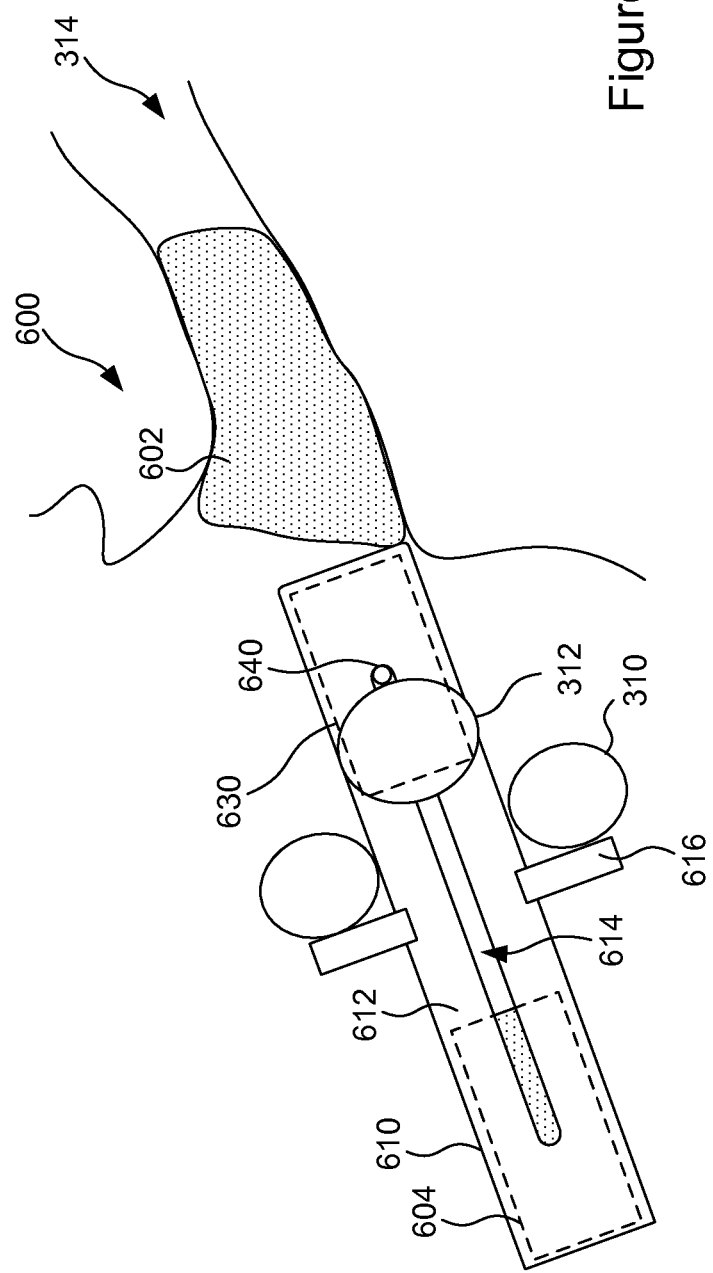
FIG. 24 is a side plan view similar to FIG. 23, but after a first earplug has been ejected from the earplug insertion device into the first ear canal.

When the device (600) is loaded with the earplugs (602 and 604), as illustrated in FIGS. 21-23, the plunger (630) can be positioned in the middle of the body housing/guide (610), and the earplugs (602 and 604) can be inserted in the housing/guide (610) on opposite sides of the plunger (630).

The parts of the device (600) can be formed from materials and by manufacturing and assembly processes similar to those described above with reference to the device (100). For example, the housing/guide (610) can be formed by an injection molding process and the plunger (630) can be formed by an extrusion process. The hole (634) in the plunger (630) can be formed by a drilling process. The plunger (630) can be placed in the housing/guide (610) with the hole (634) aligned with the slots (614) and the rod (640) can be driven through the hole (634), forming an interference fit that holds the rod (640) in place. As an example, the rod (640) may be a metal rod, such as an aluminum rod, although the rod (640) could be made of a polymer or some other type of sufficiently rigid and strong material. With the plunger (630) in place, the earplugs (602 and 604) can be inserted in opposite ends of the housing/guide (610).

Referring now to FIG. 23, the device (600) can be held with a user's two fingers (310) on opposite sides of the body (612) of the housing/guide (610) on the side of the flanges (616) adjacent to the ear canal (314). The device (600) can be positioned with the end of the housing/guide (610) that holds the first earplug (602) extending into the first ear canal (314). The user's thumb (312) can be positioned on the rod (640). The user can pull the housing/guide (610) back with the fingers (310) by applying pressure to the flanges (616), and can move the plunger (630) forward by applying pressure on the rod (640) with the thumb (312). The force of this user action causes the ejection mechanism of the device (600) to eject the first earplug (602) from the device (600) and into the first ear canal (314), as the plunger (630) plunges the first earplug (602) from the housing/guide (610) (see FIG. 24). Additional movement of the plunger (630) can be inhibited as the rod (640) reaches the end of the slots (614).

Figure 25:
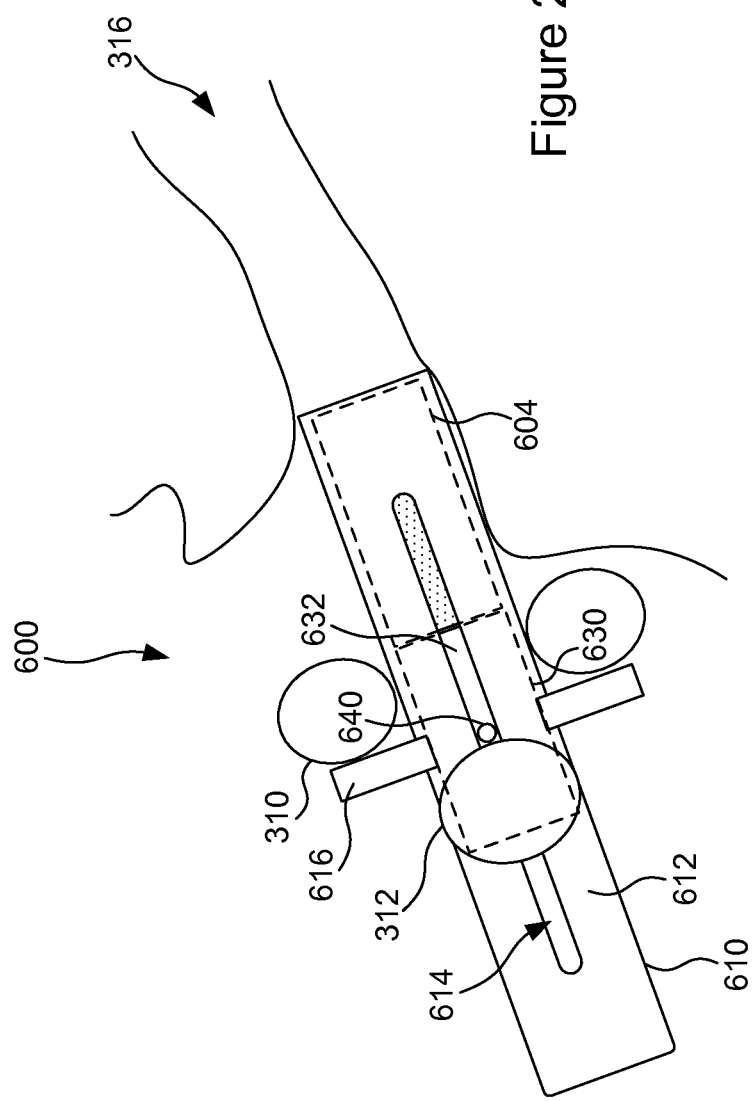
FIG. 25 is a side plan view similar to FIG. 23, but with the insertion device loaded only with a second earplug and inserted in a second ear canal.
Figure 26:
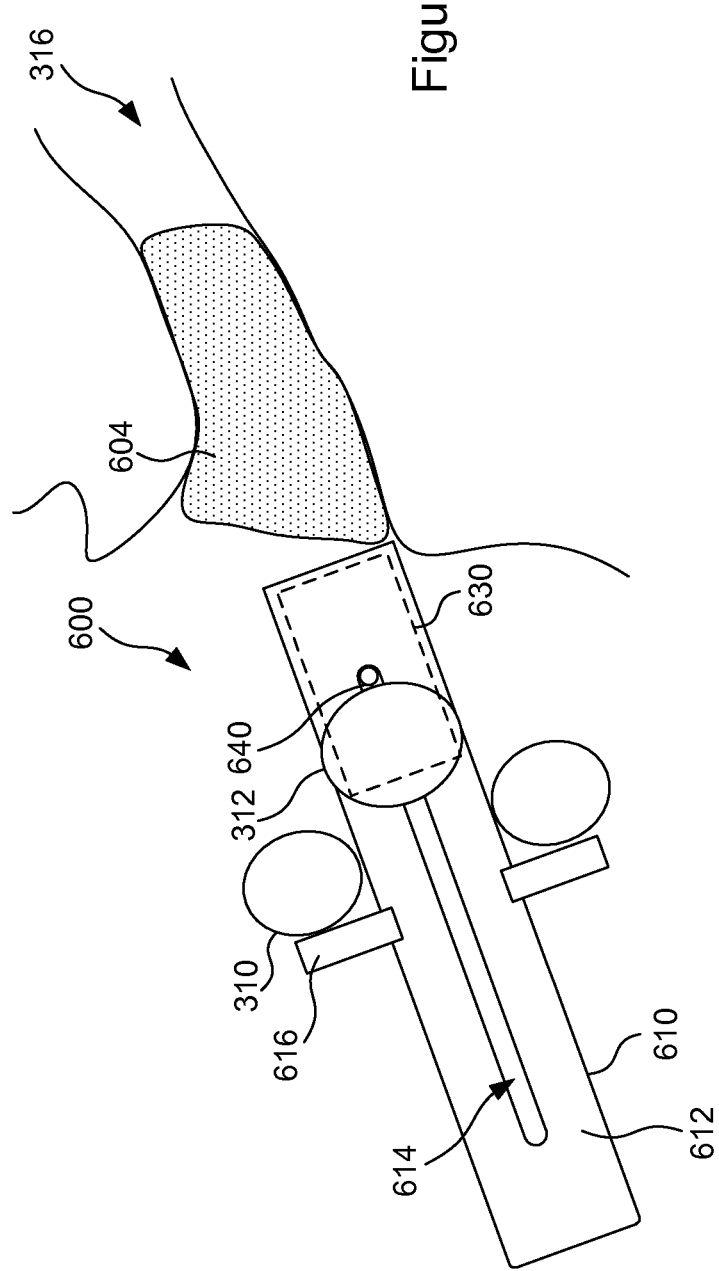
FIG. 26 is a side plan view similar to FIG. 25, but after the second earplug has been ejected from the earplug insertion device into the second ear canal.
Figure 27:
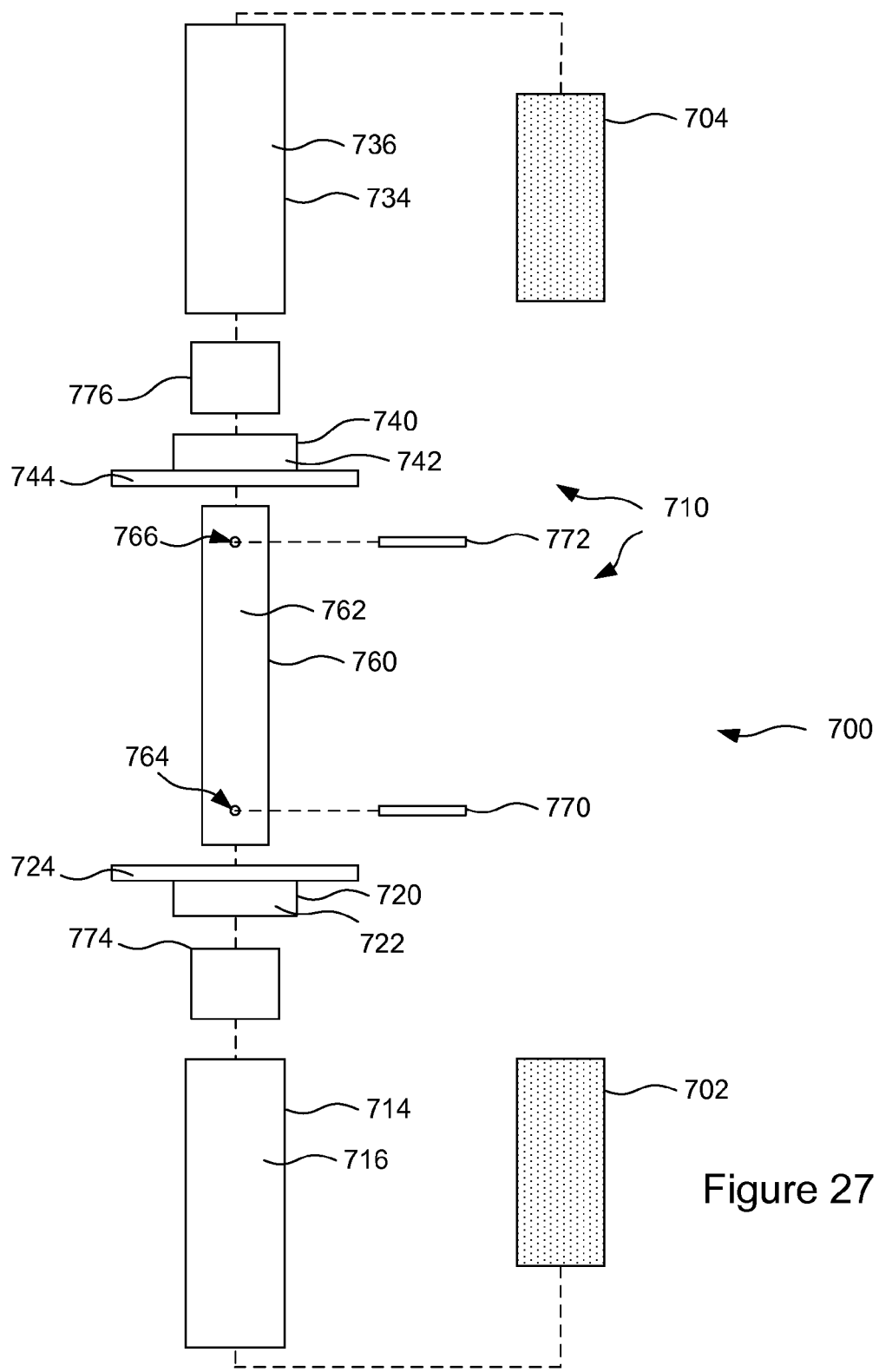
FIG. 27 is an exploded view of another described embodiment of an earplug insertion device.
Figure 28:
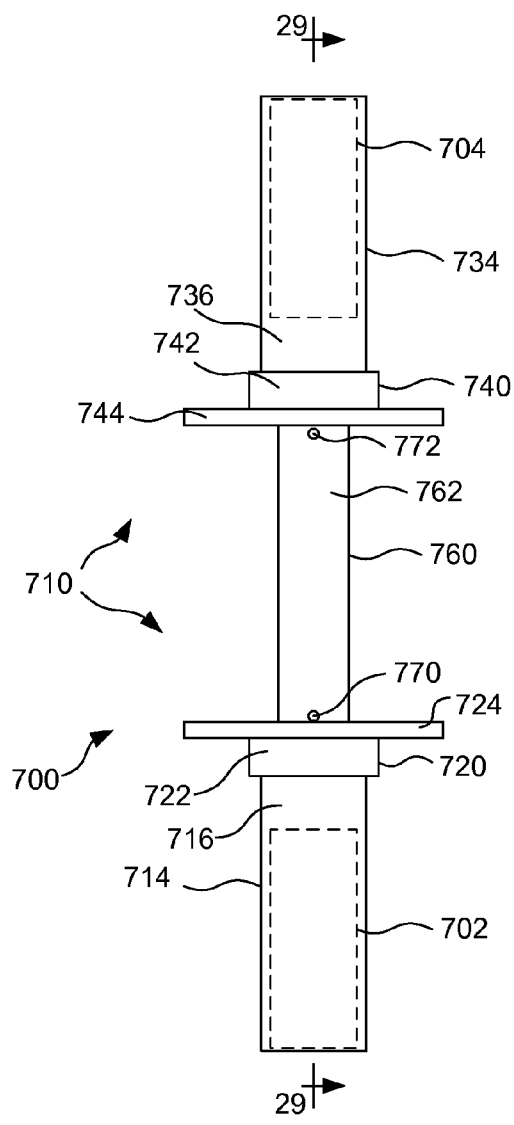
FIG. 28 is a top perspective view of the earplug insertion device of FIG. 27.
Figure 29:
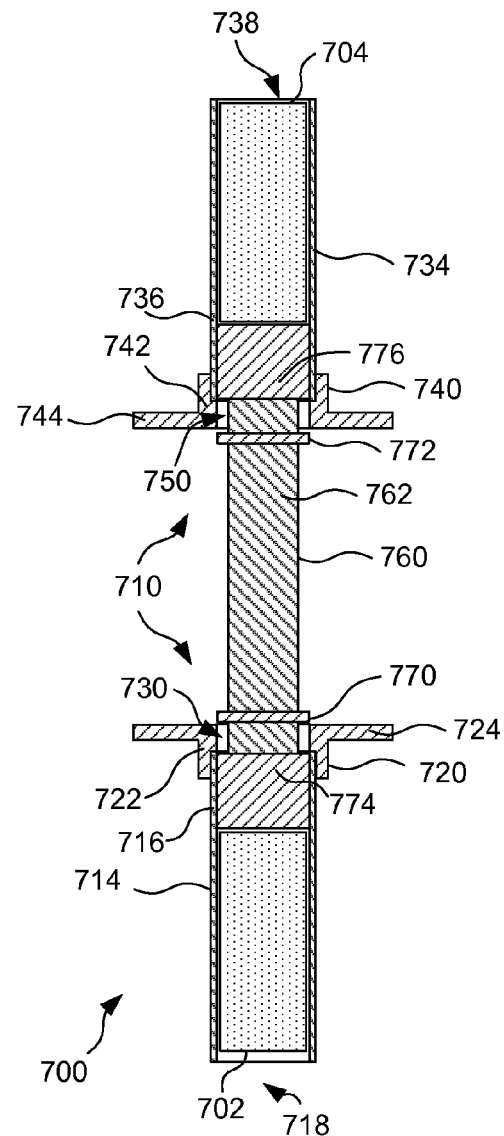
FIG. 29 is a side sectional view taken along line 29-29 of FIG. 28.
Figure 30:
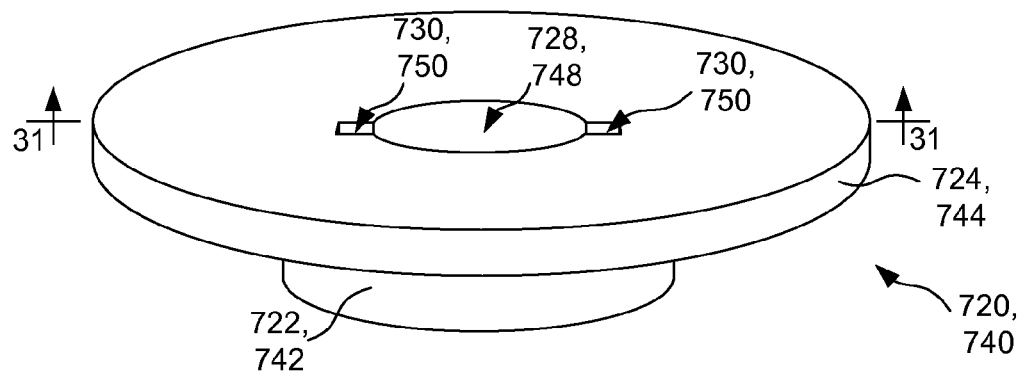
FIG. 30 is a perspective view of a cap from the earplug insertion device of FIG. 27.
Figure 31:
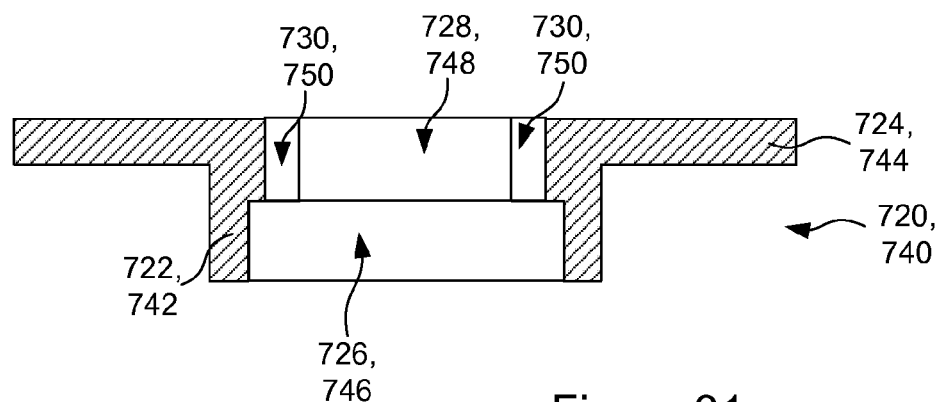
FIG. 31 is a sectional view taken along line 31-31 of FIG. 30.

As illustrated in FIG. 25, the plunger (630) can be moved back to the middle of the housing/guide (610) to where the plunger (630) abuts the second earplug (604). The end of the housing/guide (610) that holds the second earplug (604) can be inserted into the second ear canal (316). The user's two fingers (310) can be positioned on opposite sides of the body (612) of the housing/guide (610) on the side of the flanges (616) adjacent to the ear canal (316). The user's thumb (312) can be positioned on the rod (640). The user can pull the housing/guide (610) back away from the second ear canal (316) with the fingers (310) by applying pressure to the flanges (616), and can move the plunger (630) forward by applying pressure on the rod (640) with the thumb (312). The force of this user action can cause the ejection mechanism of the device (600) to eject the second earplug (604) from the device (600), as the plunger (630) plunges the second earplug (604) from the housing/guide (610) and into the second ear canal (316) (see FIG. 26).

Referring now to FIGS. 27-31, yet another alternative earplug insertion device (700) is illustrated. The device (700) can house a first earplug (702) and a second earplug (704) in a housing (710). The housing (710) can include a first guide (714) having a hollow cylindrical body (716). The body (716) can define a first exit opening (718) through which the first earplug (702) can exit the device (700). The housing can also include a first cap (720), which can include a cylindrical body (722) and a circular flange (724) extending radially out from the rear of the cylindrical body (722). The first cap (720) can define a large diameter hole (726) extending into the cylindrical body (722) on a side opposite from the circular flange (724), but not extending through the body (722). A small diameter hole (728) can extend from the large diameter hole and axially through the remainder of the body (722). The first cap (720) can also define slots (730) extending along opposite sides of the small diameter hole (728). An end of the body (716) of the first guide (714) opposite the first exit opening (718) can extend into the large diameter hole (726) in an interference fit to secure the first guide (714) and the first cap (720) together (see FIG. 29). As an alternative, the first guide (714) could be secured to the first cap (720) in some other manner, such as with an adhesive or a threaded connection. The first earplug (702) can be seated within the first guide (714) (see FIGS. 28-29).

Additionally, the housing (710) can include a second guide (734) having a hollow cylindrical body (736). The second guide cylindrical body (736) can define a second exit opening (738) through which the second earplug (704) can exit the device (700). The housing (710) can also include a second cap (740), which can include a cylindrical body (742) and a circular flange (744) extending radially out from a rear end of the cylindrical body (742). The second cap (740) can define a large diameter hole (746) extending into the cylindrical body (742) on a side opposite from the circular flange (744), but not extending through the body (742). A small diameter hole (748) can extend from the large diameter hole and axially through the remainder of the body (742). The second cap (740) can also define slots (750) extending along opposite sides of the small diameter hole (748). An end of the body (736) of the second guide (734) opposite the second exit opening (738) can extend into the large diameter hole (746) in an interference fit to secure the second guide (734) and the second cap (740) together (see FIG. 29). Alternatively, the second guide (734) could be secured to the second cap (740) in some other manner, such as with an adhesive or threaded connection. The second earplug (704) can be seated within the second guide (734) (see FIGS. 28-29).

The device (700) can also include a plunger (760). The plunger (760) can include a generally cylindrical body (762) that defines a radially-extending first hole (764) near one end of the body (762) and a radially-extending second hole (766) near a second end of the body (762) opposite the first end. A first rod (770) can extend through the first hole (764) and protrude from opposite sides of the first hole (764), and a second rod (772) can extend through the second hole (766) and protrude from opposite sides of the second hole (766). A first circular flange (774) can extend radially out from the first end of the body (762) and a second circular flange (776) can extend radially out from the second end of the body (762). The first and second flanges (774 and 776) can be formed by separate disk-shaped members that are secured to the body (762), such as with adhesives, threaded fasteners, or threaded connections.

When the device (700) is loaded with earplugs (702 and 704), the plunger body (762) can extend through the small diameter holes (728 and 748) of the first and second caps (720 and 740), respectively. The small diameter holes (728 and 748) can be sized so that the plunger body (762) can slide easily within the small diameter holes (728 and 748). The first and second guides (714 and 734) can extend outward from the respective caps (720 and 740) in opposite axial directions. The circular flanges (774 and 776) of the plunger (760) can be seated within the respective bodies (716 and 736) of the guides (714 and 734), and the rods (770 and 772) of the plunger (760) can be positioned inward of the caps (720 and 740). The circular flanges (774 and 776) of the plunger (760) can be sized so that the flanges (774 and 776) do not fit through the small diameter holes (728 and 748) so that the caps (720 and 740) generally remain attached to the plunger (760). However, the flanges (774 and 776) can be small enough to easily slide within the respective cylindrical bodies (716 and 736) of the first and second guides (714 and 734). The rods (770 and 772) can be such that they cannot fit through the caps (720 and 740) unless the respective rod (770 or 772) is aligned with the slot (730 or 750) of the respective cap (720 or 740). Thus, each guide (714 and 734) can be in a locked position with the slots (730 or 750) of the corresponding cap (720 or 740) out of alignment with the corresponding rod (770 or 772), or in an unlocked position with the slots (730 or 750) of the corresponding cap (720 or 740) aligned with the corresponding rod (770 or 772).

Figure 32:
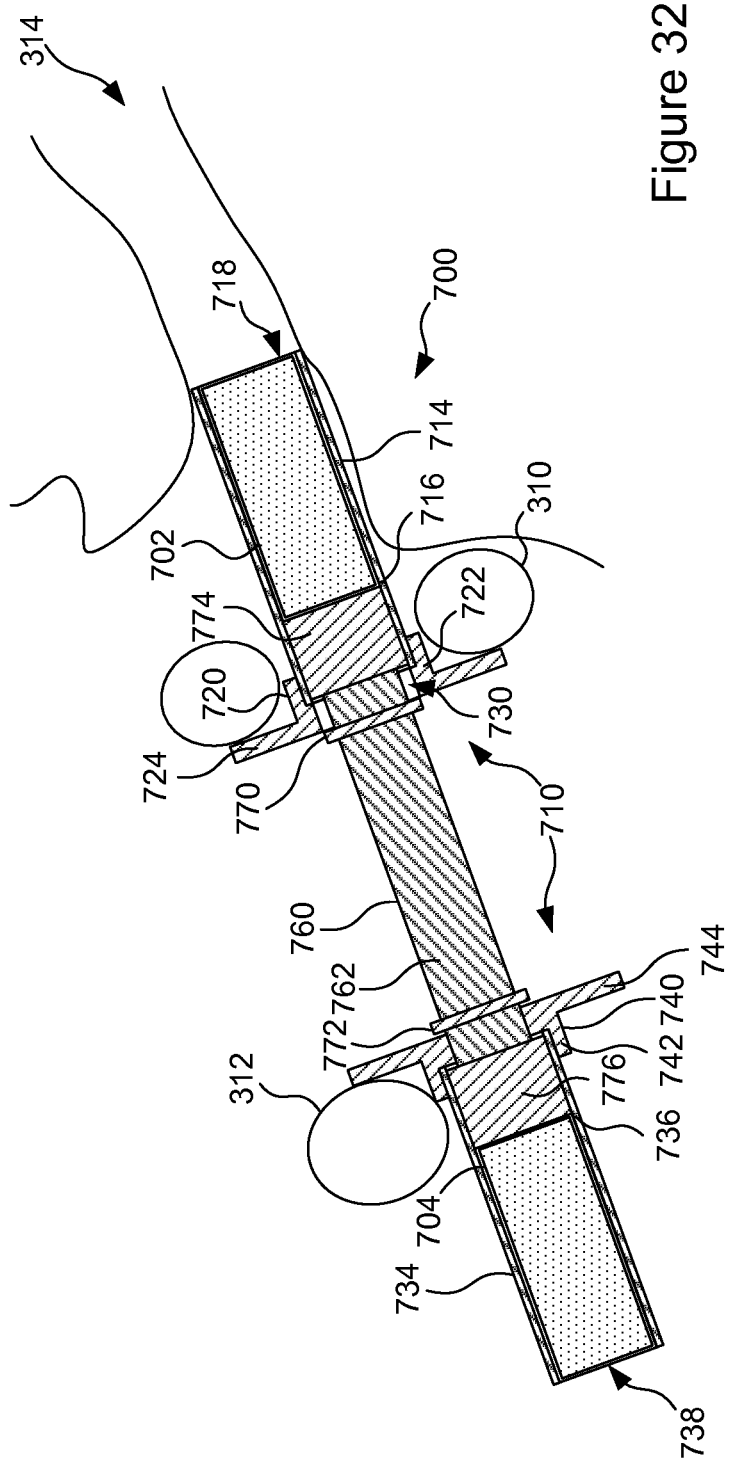
FIG. 32 is a side sectional view of the earplug insertion device of FIG. 27, illustrating the device loaded with earplugs and inserted into a first ear canal.
Figure 33:
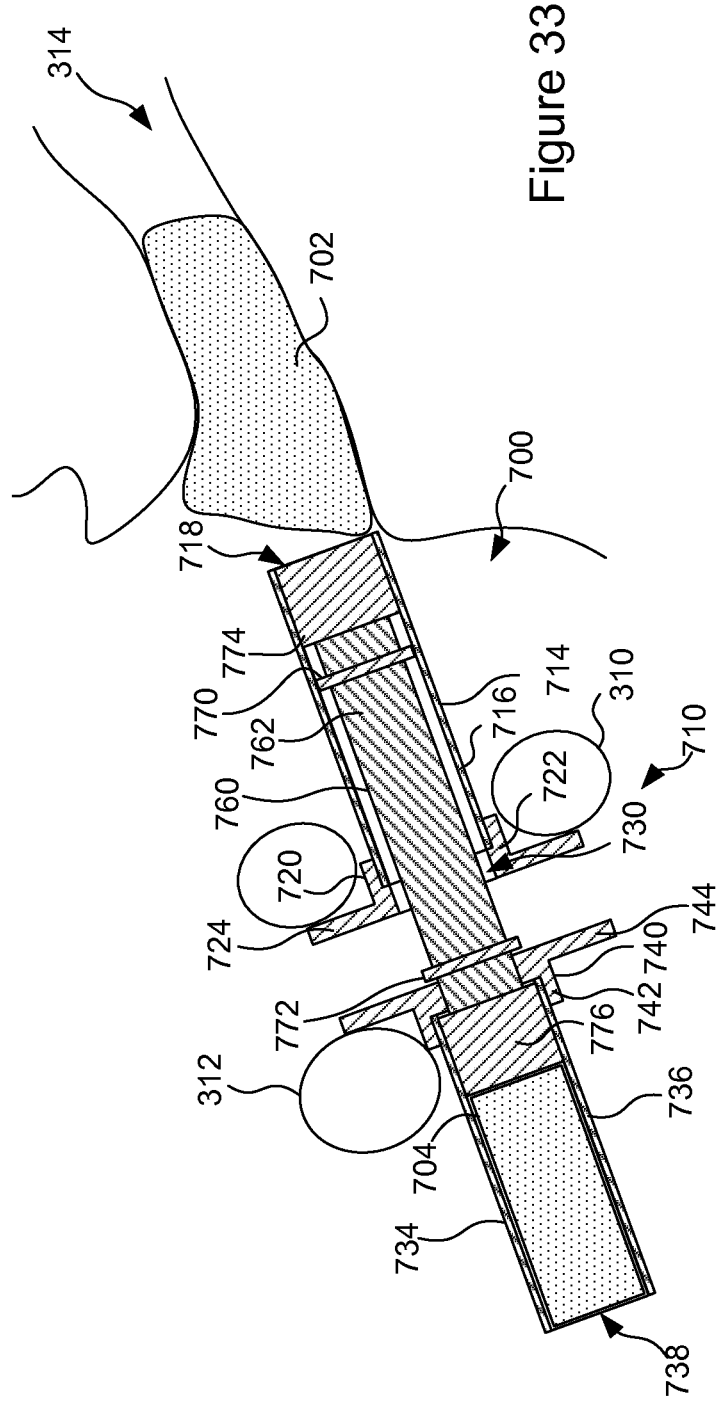
FIG. 33 is a side sectional view similar to FIG. 32, but after a first earplug has been ejected from the insertion device into the first ear canal.

Referring now to FIG. 32, with the device (700) loaded with earplugs (702 and 704), the device can be grasped with the fingers (310) on opposite sides of the first guide (714) outside of the first cap (720) (adjacent to the first ear canal (314)), and the thumb (312) on the outside of the second cap (740). The first guide (714) can be rotated to the unlocked position and the second guide (734) can be rotated to the locked position. The first guide (714) can be inserted in the first ear canal (314) until the fingers (310) abut the user's body adjacent to the first ear canal (314). The first guide (714) can be sized so that with typical sized user fingers, this insertion results in the first earplug (702) being positioned partially within the first ear canal (314), but still within the guide (714). The user can then use the fingers (310) to pull the first cap (720), and thus the first guide (714), out and away from the first ear canal (314), and use the thumb (312) to push on the second cap (740) to move the second cap (740) and the plunger (760) forward. Thus, the ejection mechanism of the device (700) can eject the first earplug (702) from the first exit opening (718) of the device (700) and into the first ear canal (314), as the plunger (760) plunges the first earplug (702) from the first guide (714) and the first guide (714) is removed from the first ear canal (314) (see FIG. 33).

Figure 34:
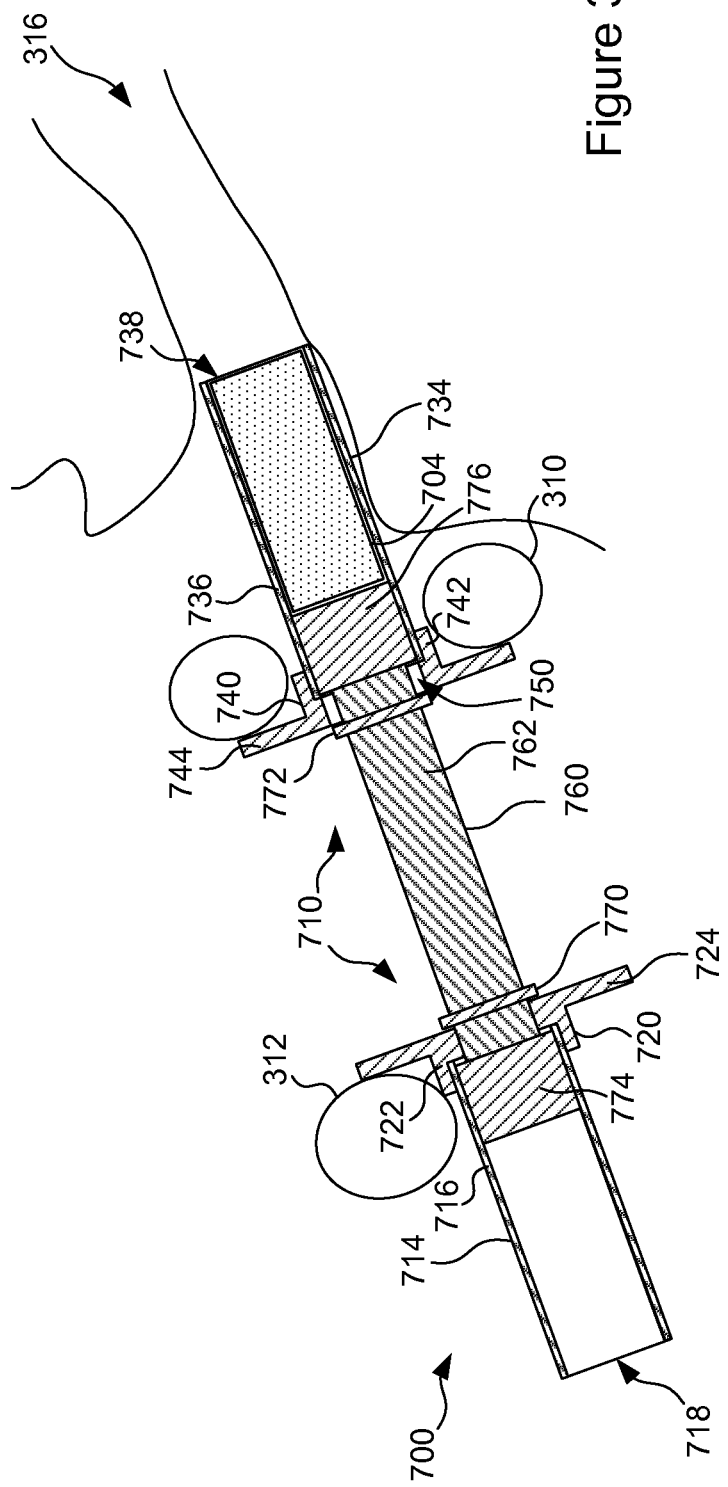
FIG. 34 is a side sectional view similar to FIG. 32, but with the insertion device loaded only with a second earplug and inserted in a second ear canal.
Figure 35:
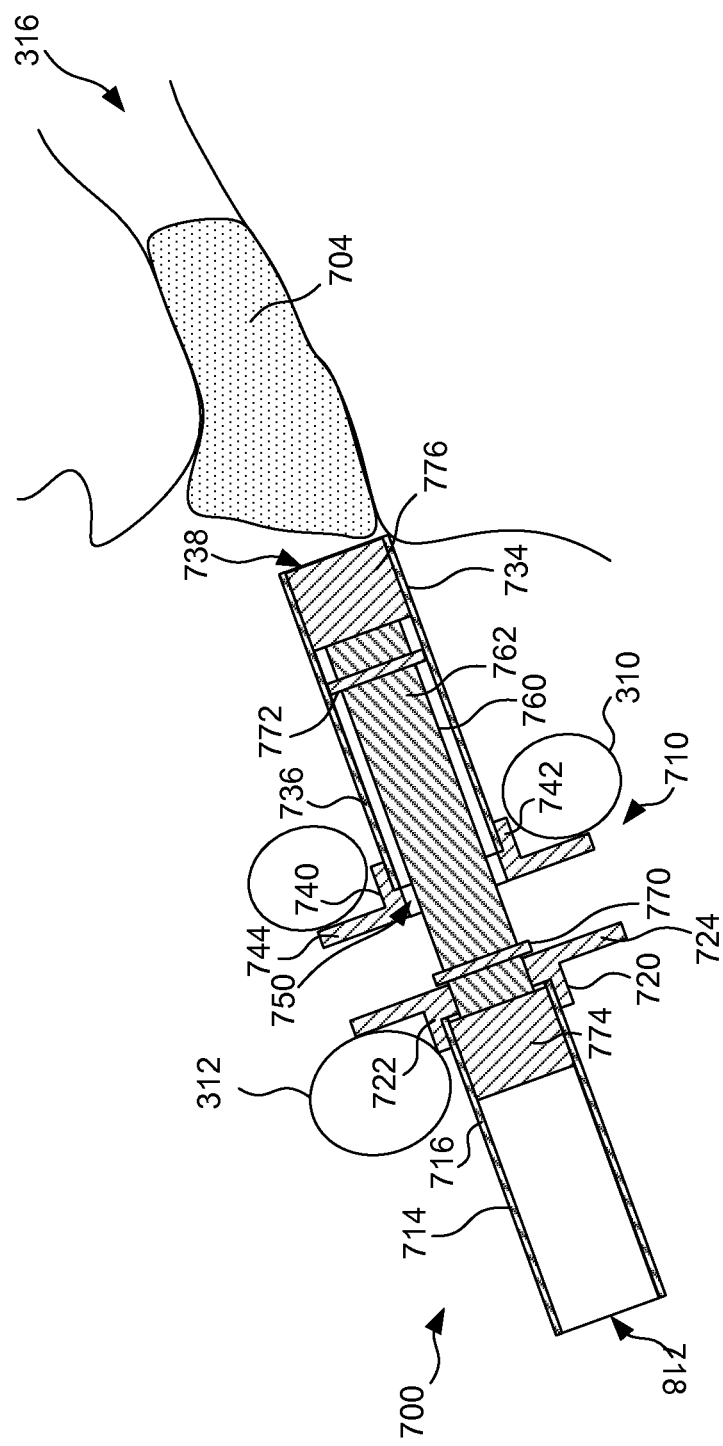
FIG. 35 is a side sectional view similar to FIG. 34, but after the second earplug has been ejected from the insertion device into the second ear canal.

The first guide (714) can be pulled away from the second guide (734). The second guide (734) can be rotated to the unlocked position, and the first guide (714) can be rotated to the locked position, as illustrated in FIG. 34. The device (700) can be grasped with the fingers (310) on opposite sides of the second guide (734) outside of the second cap (740) (adjacent to the second ear canal (316)), and the thumb (312) on the outside of the first cap (720). The second guide (734) can be inserted in the second ear canal (316) until the fingers (310) abut the user's body adjacent to the second ear canal (316). The second guide (734) can be sized so that with typical sized user fingers, this insertion results in the second earplug (704) being positioned partially within the second ear canal (316), but still within the guide (734). The user can then use the fingers (310) to pull the second cap (740), and thus the second guide (734), out and away from the second ear canal (316), and use the thumb (312) to push on the first cap (720) to move the first cap (720) and the plunger (760) forward. Thus, in response to force from the user, the ejection mechanism of the device (700) eject the second earplug (704) from the second exit opening (738) of the device (700), as the plunger (760) plunges the second earplug (704) from the second guide (734) and the second guide (734) is removed from the second ear canal (316) (see FIG. 35).

The earplug insertion device (700) can be made using similar materials and manufacturing techniques to those described above. The caps (720 and 740) may be placed on the plunger body (762) prior to one or both of the plunger flanges (774 and 776) being placed on the body (762) because the caps (720 and 740) may not fit over the flanges (774 and 776). As with all the insertion device designs discussed herein, many different alterations to the design of the insertion device (700) could be implemented. For example, the plunger (760) could be molded with knobs, rather than having rods (770 and 772) extending through the plunger body (762).

The device (700) could be modified by having only a single rod passing radially through the mid-point of the plunger, and omitting the caps (720 and 740). The plunger could be longer than the plunger (720) and could have a constant diameter throughout its length. In addition, the length of the rod could be greater than the diameter of the guides (714 and 734). A distance from the rod to each end of the plunger could be about the same as the length of a guide. Thus, the plunger could be extended in either direction to plunge the appropriate earplug from the device, and the rod could keep the plunger from extending too far into either guide.

In the embodiments described above, the housing of the device can be part of the ejection mechanism that responds to a user force by ejecting one or more earplugs. For example, in several of the embodiments, one or more guides are part of the housing. However, those guides guide the movement of a plunger that ejects an earplug from the earplug insertion device and into an ear canal, thereby forming part of the ejection mechanism. Guides that are part of the housing can also act as plungers in some devices. In addition, the housing can be formed of multiple connected parts, and those parts of the housing can be separated, as in the embodiment illustrated in FIGS. 27-35.

Figure 36:
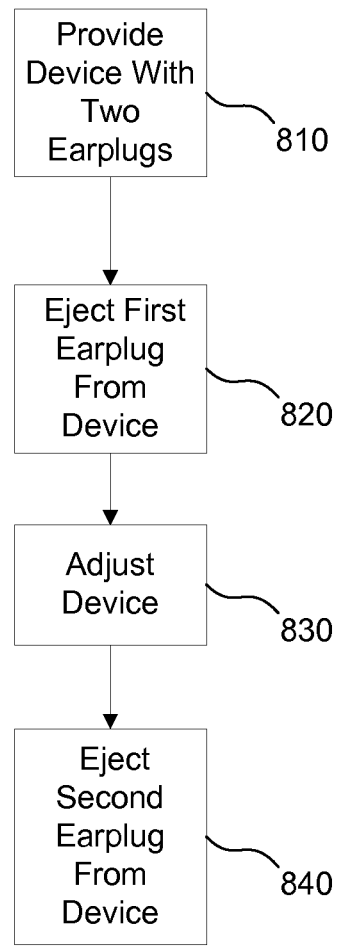
FIG. 36 is a flowchart illustrating a general method of inserting a pair of earplugs.

Referring now to FIG. 36, a general method of inserting a pair of earplugs is described. A device holding two earplugs is provided (810). The device can be one of the devices described above or some other device. The term providing or provided is used broadly herein to refer to any way of providing a device to be used, such as, without limitation, making the device, buying or selling the device for use, or selecting a device to be used. As an example, providing the device can include selecting a device and inserting a removable casing at least partially into the device, where the casing holds the first earplug and the second earplug. A first earplug can be ejected (820) from the device and into an ear canal. This can be done in a first motion. Ejecting the first earplug can include inserting the earplug insertion device at least partially into the first ear canal and removing the earplug insertion device from the first ear canal while ejecting the first earplug. In some embodiments, the device may be adjusted (830) to allow a second earplug to be ejected. Adjusting may include moving one or more parts of the earplug insertion device in an adjustment direction that is different from a first ejection direction of the first ejection motion. For example, after a plunger is moved in an axial direction to eject the first earplug, the plunger may be moved in the opposite axial direction or rotated to a position where the plunger can be moved to eject the second earplug. A second earplug may be ejected (840) from the device into a second ear canal. This may be done in a second motion. The second ear canal may be the same ear canal later in time, the other ear canal for the same person, or some other person's ear canal. In addition, a user may use a device to eject earplugs into the person's own ear canals and/or into another person's ear canals.

The subject matter defined in the appended claims is not necessarily limited to the benefits described herein. A particular implementation of the invention may provide all, some, or none of the benefits described herein. Although operations for the various techniques are described herein in a particular, sequential order for the sake of presentation, it should be understood that this manner of description encompasses rearrangements in the order of operations, unless a particular ordering is required. For example, operations described sequentially may in some cases be rearranged or performed concurrently. Techniques described herein with reference to flowcharts may be used with one or more of the systems described herein and/or with one or more other systems. Moreover, for the sake of simplicity, flowcharts may not show the various ways in which particular techniques can be used in conjunction with other techniques.

While the invention has been particularly shown and described with reference to preferred embodiments thereof, it will be understood by those skilled in the art that various changes in form and details may be made therein without departing from the spirit and scope of the invention. For example, the cylindrically-shaped parts described herein could be other shapes, such as substantially-cylindrical shapes with oval cross sections, shapes with rectangular cross sections, etc.

We claim:

1. An earplug insertion device, comprising:
    a housing that is configured to hold a first earplug and a second earplug; and
    an ejection mechanism that is configured to respond to a first user force by ejecting the first earplug from the device in a first ejection motion, the ejection mechanism also being configured to respond to a second user force by ejecting the second earplug from the device in a second ejection motion, the ejection mechanism comprising:
        a first guide configured to hold the first earplug;
        a second guide configured to hold the second earplug and to slide at least partially into the first guide to eject the first earplug from the first guide; and
        a plunger configured to slide relative to the first guide and to slide at least partially into the second guide to eject the second earplug from the second guide.

2. The device of claim 1, wherein the device comprises a removable casing configured to hold at least one of the first and second earplugs.

3. The device of claim 2, wherein the casing is configured to hold both of the first and second earplugs.

4. The device of claim 1, wherein at least one of the first and second guides is part of the housing and part of the ejection mechanism.

5. The device of claim 1, wherein the ejection mechanism is configured to inhibit additional movement beyond the first ejection motion, and to inhibit additional movement beyond the second ejection motion.

6. The device of claim 1, wherein the housing is configured to extend at least partially into a human ear canal.

7. The device of claim 1, wherein the housing comprises a flexible material.

8. The device of claim 1, wherein the plunger is slidable at least partially into the first guide and the second guide.

9. The device of claim 1, wherein the ejection mechanism is configured to eject the first earplug and the second earplug from one exit opening.

10. The device of claim 1, wherein:
    the ejection mechanism is configured to inhibit movement beyond the first ejection motion until a user applies a release force;
    the ejection mechanism is configured to respond to the release force with a release movement that frees the mechanism to move beyond the first ejection motion; and
    the second ejection motion moves the mechanism beyond the first ejection motion.

11. The device of claim 1, wherein the first guide is configured to hold the first earplug at least partially within the first guide.

12. The device of claim 1, wherein the second guide is configured to hold the second earplug at least partially within the second guide.

13. An earplug insertion casing, comprising:
    a first guide holding a first earplug at least partially within the first guide; and
    a second guide slidably moveable relative to the first guide, the second guide holding a second earplug at least partially within the second guide;
    wherein the second guide is slidably moveable to eject the first earplug from the first guide.

14. The casing of claim 13, wherein the second guide comprises a substantially cylindrical section that is at least partially slidably inserted in the first guide.

15. The casing of claim 13, wherein the first and second guides each comprise a substantially cylindrical section.

16. A method comprising:
    providing an earplug insertion device holding a first earplug at least partially within a first guide and a second earplug at least partially within a second guide;
    ejecting a first earplug from the earplug insertion device and into a first ear canal, ejecting the first earplug comprising slidably moving the second guide relative to the first guide to eject the first earplug from the first guide; and
    ejecting the second earplug from the earplug insertion device and into a second ear canal.

17. The method of claim 16, wherein ejecting the first earplug comprises a first ejection motion of the earplug insertion device, wherein ejecting the second earplug comprises a second ejection motion of the earplug insertion device, and wherein the method further comprises adjusting the earplug insertion device after the first ejection motion to allow the second ejection motion.

18. The method of claim 17, wherein adjusting comprises moving the earplug insertion device in an adjustment direction that is different from a first ejection direction of the first ejection motion.

19. The method of claim 16, further comprising inserting the earplug insertion device at least partially into the first ear canal prior to ejecting the first earplug.

20. The method of claim 19, further comprising pulling at least part of the earplug insertion device from the first ear canal while ejecting the first earplug.

21. The method of claim 16, wherein the first ear canal and the second ear canal are different ear canals.

22. The method of claim 16, wherein the first ear canal and the second ear canal are the same ear canal.

23. The method of claim 16, wherein providing the earplug insertion device comprises inserting a removable casing at least partially into the earplug insertion device, the casing holding the first earplug and the second earplug.

24. The method of claim 16, wherein ejecting the first earplug comprises sliding a plunger relative to the first guide, and wherein ejecting the second earplug comprises sliding the plunger relative to the second guide.

* * * * *